(12) United States Patent
Dodd et al.

(10) Patent No.: US 11,938,261 B2
(45) Date of Patent: Mar. 26, 2024

(54) FLUID FLOW-THROUGH

(71) Applicant: Terumo BCT Biotechnologies, LLC, Lakewood, CO (US)

(72) Inventors: Jon A. Dodd, Littleton, CO (US); Daniel R. Clement, Golden, CO (US); Dennis J. Hlavinka, Arvada, CO (US); Jeremy T. Parsons, Denver, CO (US); Haralambos P. Apostolopoulos, Castle Rock, CO (US)

(73) Assignee: Terumo BCT Biotechnologies, LLC, Lakewood, CO (US)

( * ) Notice: Subject to any disclaimer, the term of this patent is extended or adjusted under 35 U.S.C. 154(b) by 961 days.

(21) Appl. No.: 16/523,972

(22) Filed: Jul. 26, 2019

(65) Prior Publication Data

US 2020/0030520 A1 Jan. 30, 2020

Related U.S. Application Data

(60) Provisional application No. 62/829,815, filed on Apr. 5, 2019, provisional application No. 62/711,283, filed on Jul. 27, 2018.

(51) Int. Cl.
*B01L 3/00* (2006.01)
*A61L 2/00* (2006.01)
(Continued)

(52) U.S. Cl.
CPC .......... *A61M 1/3681* (2013.01); *A61L 2/0011* (2013.01); *A61M 1/3455* (2013.01); *A61M 1/3683* (2014.02); *A61M 1/3689* (2014.02); *B01L 3/502* (2013.01); *A61K 41/10* (2020.01); *A61M 2206/10* (2013.01);
(Continued)

(58) Field of Classification Search
CPC .... A61K 41/10; A61L 2/0011; A61M 1/0209; A61M 1/3455; A61M 1/3681; A61M 1/3683; A61M 1/3689; A61M 2202/20; A61M 2206/10; B01L 2300/0877;
(Continued)

(56) References Cited

U.S. PATENT DOCUMENTS 3,628,445 A 12/1971 Weber
3,926,556 A 12/1975 Boucher
(Continued)

FOREIGN PATENT DOCUMENTS

EP 3434295 A1 1/2019
GB 2200020 A1 7/1988
(Continued)

OTHER PUBLICATIONS

International Search Report and Written Opinion, PCT/US2019/043808, dated Mar. 11, 2020.
(Continued)

*Primary Examiner* — Dirk R Bass
(74) *Attorney, Agent, or Firm* — Harness, Dickey & Pierce, P.L.C.

(57) ABSTRACT

Embodiments are described for treating a fluid, e.g., a biological fluid. The embodiments may include systems, apparatuses, and methods. Embodiments may provide for a flow cell, with a plurality of manipulation elements, through which a fluid is flowed. The fluid may be treated (e.g., exposed to energy) as it moves through the flow cell. In embodiments, the flow cell may be used to inactivate pathogens in the fluid.

17 Claims, 22 Drawing Sheets

(51) Int. Cl.
*A61M 1/34* (2006.01)
*A61M 1/36* (2006.01)
*A61K 41/10* (2020.01)

(52) U.S. Cl.
CPC ............... *B01L 2300/0877* (2013.01); *B01L 2300/0883* (2013.01); *B01L 2300/12* (2013.01); *B01L 2300/123* (2013.01)

(58) Field of Classification Search
CPC ......... B01L 2300/0883; B01L 2300/12; B01L 2300/123; B01L 3/502
See application file for complete search history.

(56) References Cited

U.S. PATENT DOCUMENTS

| | | |
|---|---|---|
| 4,464,166 A | 8/1984 | Edelson |
| 4,676,896 A | 6/1987 | Norton |
| 4,708,715 A | 11/1987 | Troutner et al. |
| 4,737,140 A | 4/1988 | Lee et al. |
| 4,952,812 A | 8/1990 | Miripol et al. |
| 5,190,766 A | 3/1993 | Ishihara |
| 5,399,719 A | 3/1995 | Wollowitz et al. |
| 5,702,432 A | 12/1997 | Chen et al. |
| 5,770,147 A | 6/1998 | Müller |
| 5,789,150 A | 8/1998 | Margolis-Nunno et al. |
| 5,827,644 A | 10/1998 | Floyed et al. |
| 6,113,566 A | 9/2000 | Schleicher |
| 6,312,593 B1 | 11/2001 | Petrie |
| 6,368,462 B1 | 4/2002 | Lumiala et al. |
| 6,756,597 B2 | 6/2004 | Avnery et al. |
| 6,773,608 B1 | 8/2004 | Hallett et al. |
| 6,951,548 B1 | 10/2005 | Einstein |
| 7,361,427 B1 | 4/2008 | Dow et al. |
| 7,422,910 B2 | 9/2008 | Fitzgerald et al. |
| 7,479,123 B2 | 1/2009 | Briggs |
| 7,498,156 B2 | 3/2009 | Goodrich et al. |
| 7,743,928 B2 | 6/2010 | Crowley et al. |
| 7,753,869 B2 | 7/2010 | Davidner et al. |
| 8,057,418 B2 | 11/2011 | Korbling et al. |
| 8,420,022 B2 | 4/2013 | Soler et al. |
| 8,556,844 B2 | 10/2013 | Leonard |
| 8,591,486 B2 | 11/2013 | Locke et al. |
| 8,703,467 B2 | 4/2014 | Reiter et al. |
| 9,044,523 B2 | 6/2015 | Hlavinka et al. |
| 9,265,876 B1 | 2/2016 | Ben-Hur |
| 9,603,989 B2 | 3/2017 | Brown |
| 10,301,195 B2 | 5/2019 | Smetona et al. |
| 2003/0060747 A1 | 3/2003 | Fries et al. |
| 2003/0113704 A1 | 6/2003 | Stassinopoulos et al. |
| 2003/0138346 A1 | 7/2003 | Gunn et al. |
| 2003/0156992 A1 | 8/2003 | Anderson et al. |
| 2004/0127840 A1 | 7/2004 | Gara et al. |
| 2004/0206408 A1 | 10/2004 | Peters et al. |
| 2004/0256326 A1 | 12/2004 | Hannon et al. |
| 2009/0318302 A1 | 12/2009 | Delamarche et al. |
| 2010/0203610 A1 | 8/2010 | Zhou et al. |
| 2010/0326916 A1 | 12/2010 | Wrazel et al. |
| 2011/0021966 A1 | 1/2011 | Leonard |
| 2012/0219633 A1 | 8/2012 | Sowemimo |
| 2014/0097353 A1 | 4/2014 | Ben-Hur et al. |
| 2016/0038904 A1 | 2/2016 | Arora et al. |
| 2016/0296943 A1 | 10/2016 | Ladtkow et al. |
| 2016/0334312 A1 | 11/2016 | Gaitas et al. |
| 2017/0021042 A1 | 1/2017 | Dodd et al. |
| 2019/0099543 A1 | 4/2019 | Sasaki |

FOREIGN PATENT DOCUMENTS

| | | |
|---|---|---|
| WO | 03063915 A1 | 8/2003 |
| WO | 2005118000 A1 | 12/2005 |

OTHER PUBLICATIONS

Commenge et al., "Optimal Design for Flow Uniformity in Microchannel Reactors," AIChE Journal, vol. 48, No. 2, pp. 345-358 (Feb. 2002).

Delsman et al., "Microchannel Plate Geometry Optimization for Even Flow Distribution at High Flow Rates," Trans. IChemE Part A, Chemical Engineering Research and Design, 82(A2), pp. 267-275 (Feb. 2004).

Griffini et al., "Effect of Microchannel Plate Design on Fluid Flow Uniformity at Low Flow Rates," Chem. Eng. Technol. 2007, 30, No. 3, pp. 395-406.

Pan et al., "Optimal Design of Complex Manifold Geometries for Uniform Flow Distribution Between Microchannels," Chem. Eng. J. 137, 2008, pp. 339-346.

Henschler, R., et al., Development of S-303 Pathogen Inactivation Technology for Red Blood Cell Concentrates, Transfusion Medicine and Hemotherapy, 38:33-42 (2011).

Invitation to Pay Additional Fees and Partial International Search Result and Provisional Opinion, PCT/US2019/043808, dated Nov. 6, 2019.

Zhu et al., "The Effectiveness of Riboflavin Photochemical-Mediated Virus Inactivation and Changes in Protein Retention in Fresh-Frozen Plasma Treated Using a Flow-Based Treatment Device", Transfusion, Jan. 2015, vol. 55, pp. 100-107.

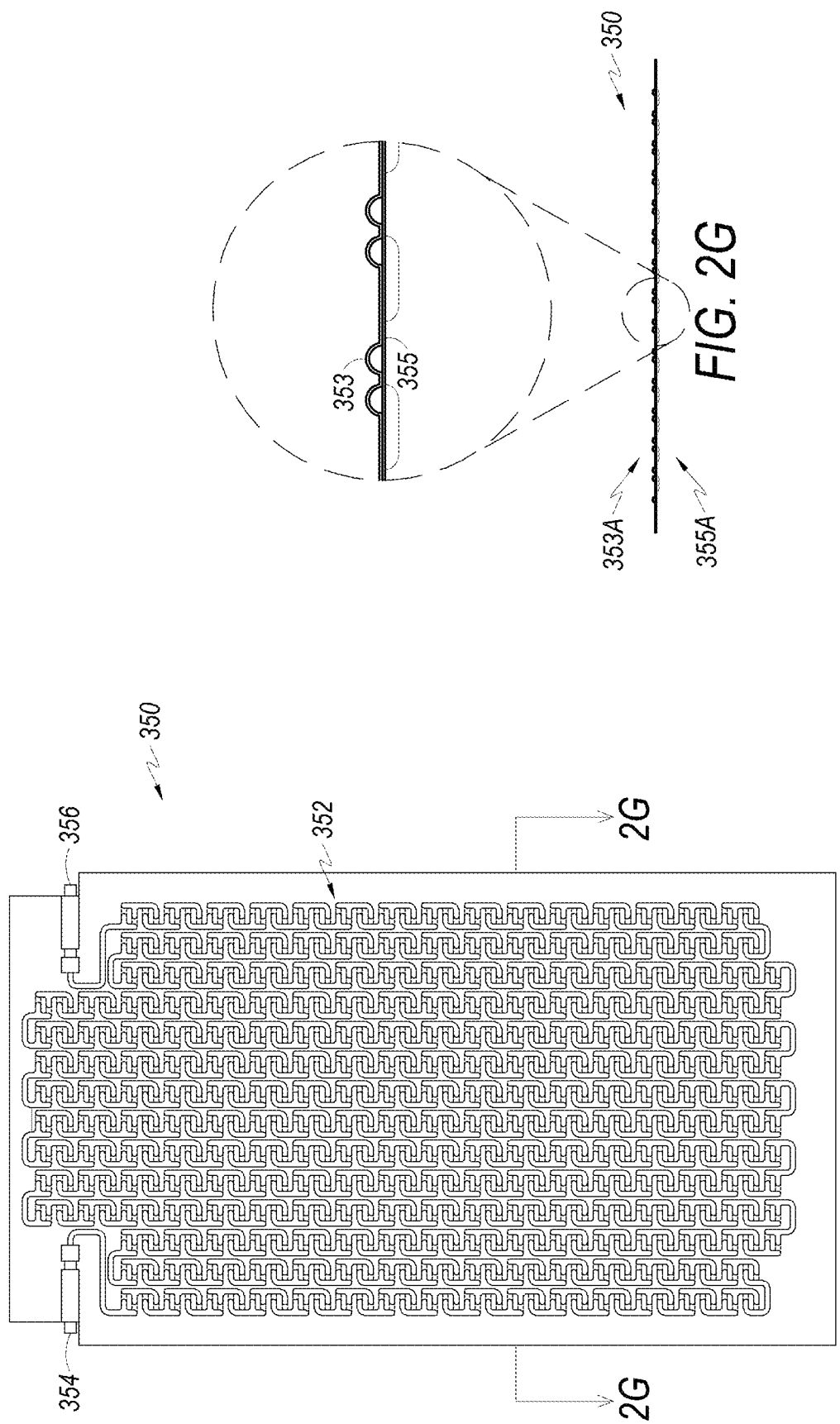

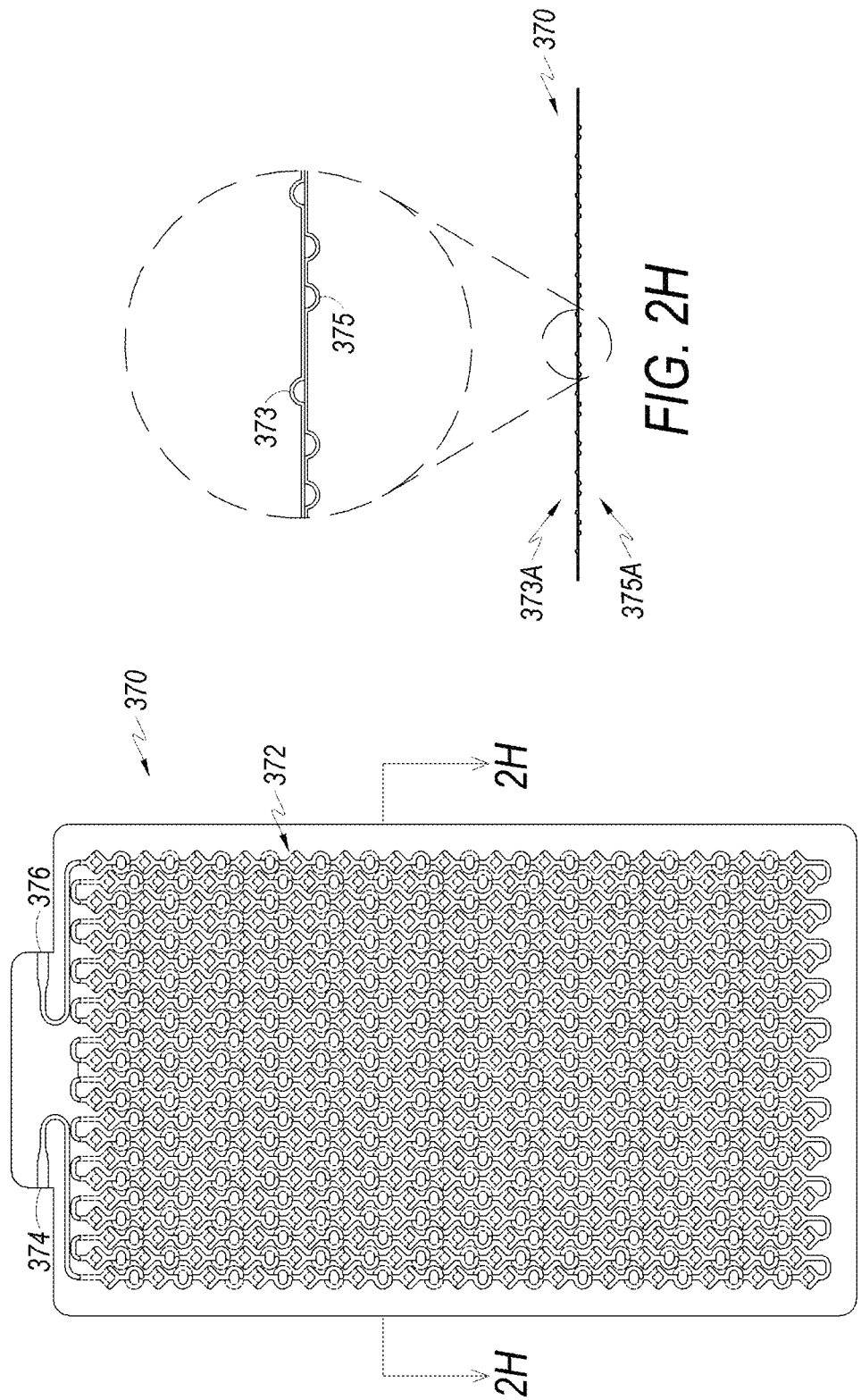

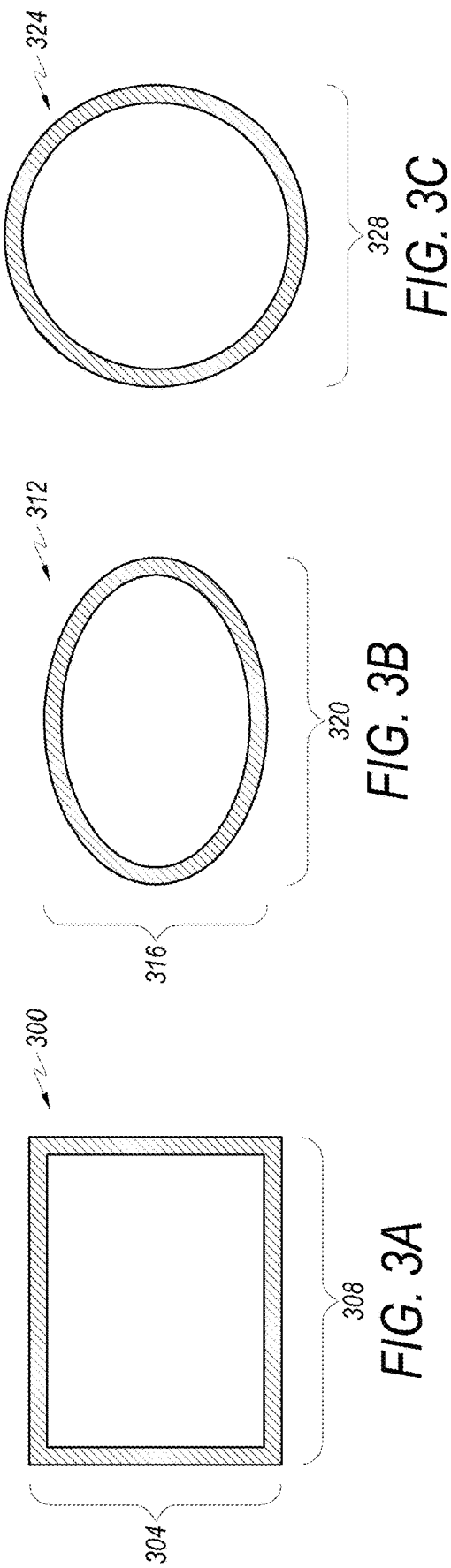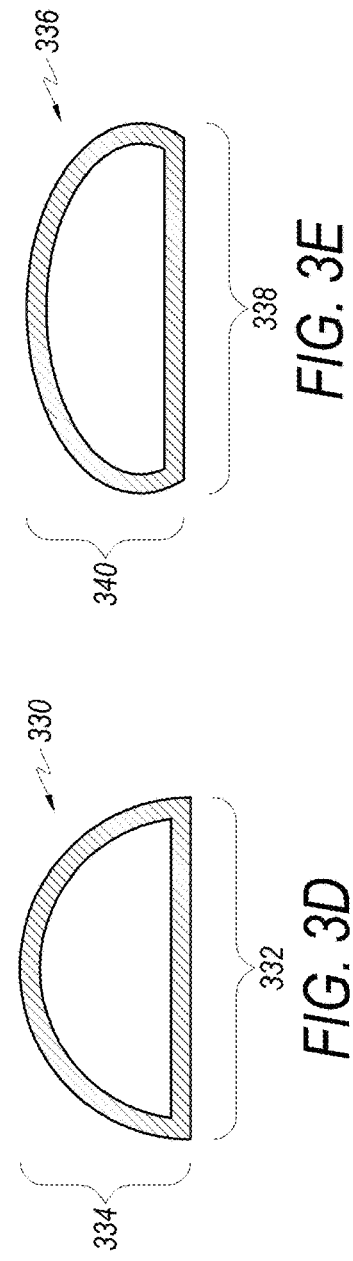

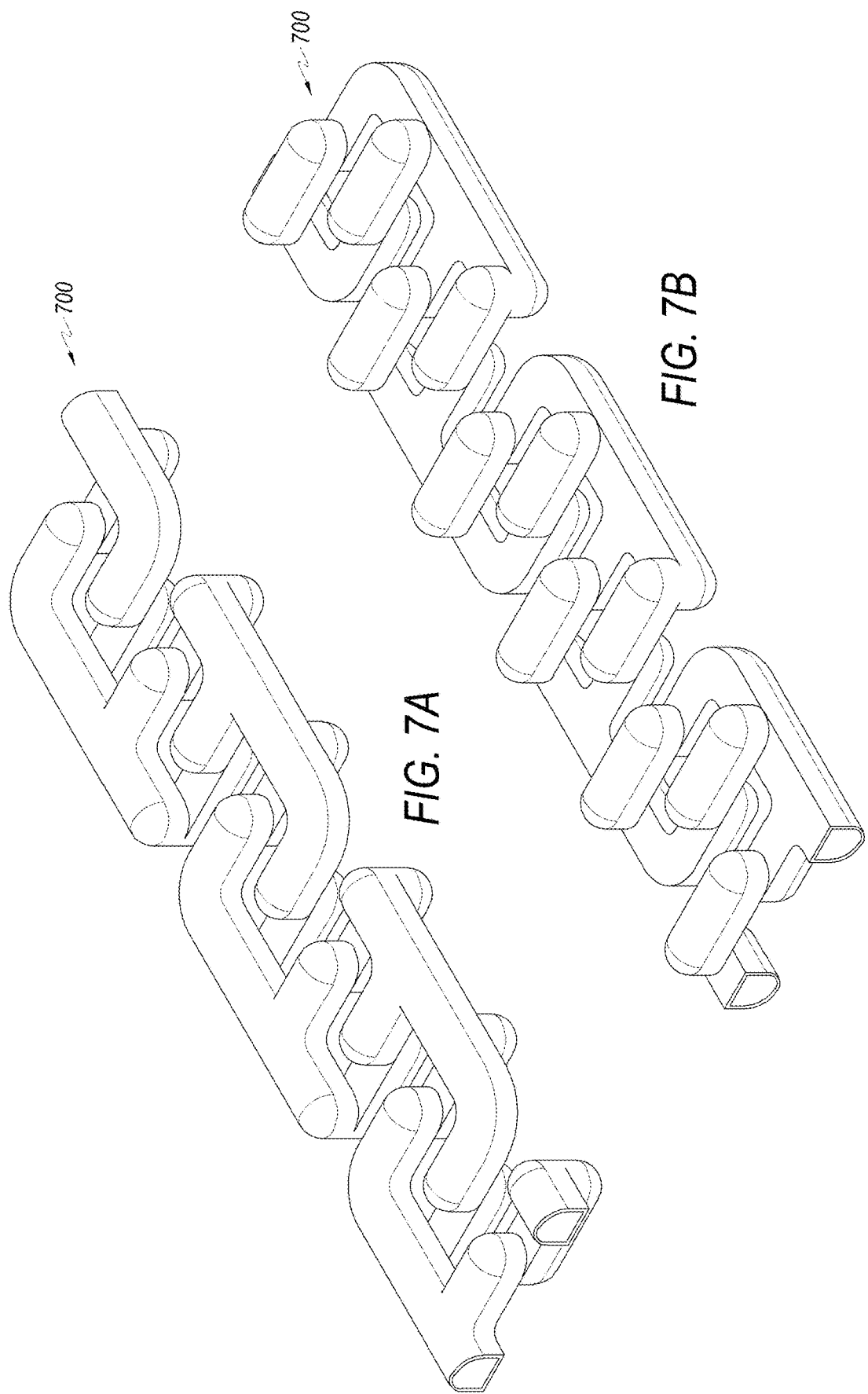

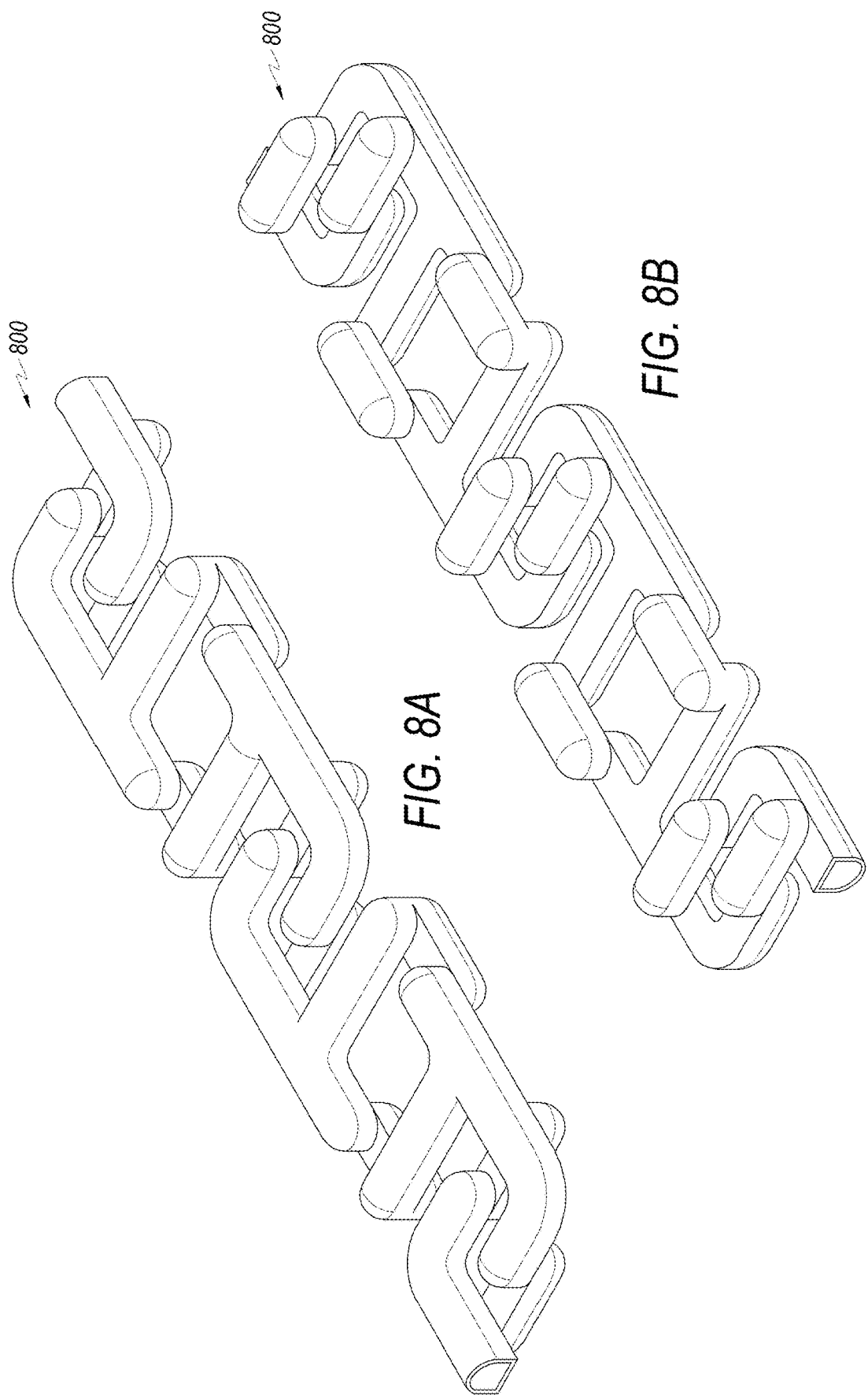

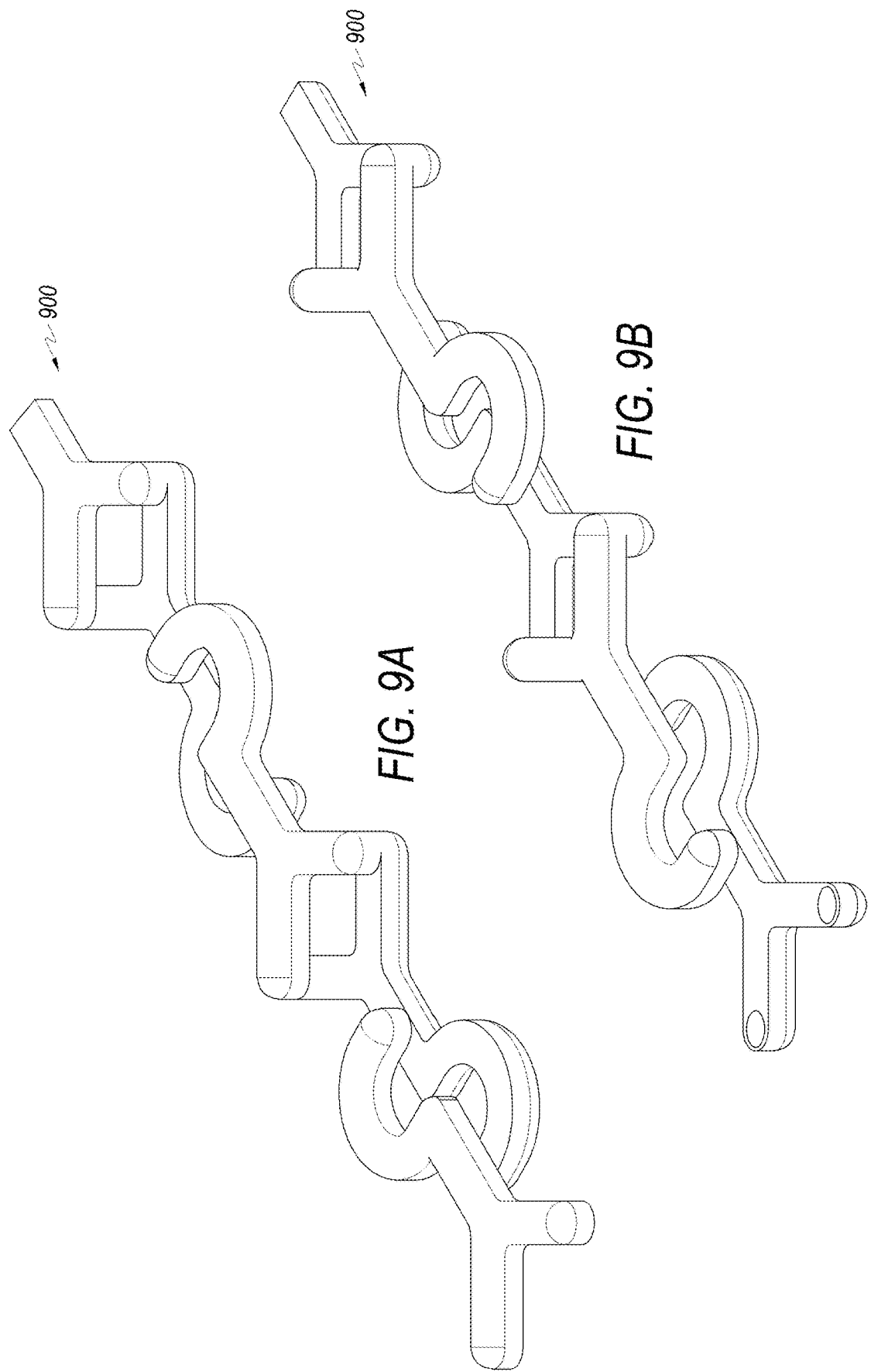

FLUID FLOW-THROUGH

CROSS-REFERENCE TO RELATED APPLICATION(S)

This patent application claims priority to U.S. Provisional Patent Application No. 62/711,283 entitled "FLUID FLOW-THROUGH AND MIX," filed Jul. 27, 2018 and also claims priority to U.S. Provisional Patent Application No. 62/829,815 entitled "FLUID FLOW-THROUGH," filed Apr. 5, 2019, both of the above-identified patent applications are hereby incorporated by reference in their entirety as if set forth herein in full.

BACKGROUND

There is a constant need for treating fluids. Treatments may involve several physical or chemical processes that may include modifying components in a fluid, adding components to a fluid, removing components from a fluid, manipulating fluid, adding energy to a fluid, removing energy from a fluid, bringing components of a fluid into intimate contact, mixing fluid, distributing components of fluid, etc. One example of when fluid may be treated is to pathogen reduce a biological fluid to safely administer the biological fluid to patients without the risk of infection. For example, blood and blood components may contain pathogens that when infused into a patient may infect the patient. To prevent this, the biological fluid may be treated to reduce pathogens in the blood or blood components. Another example may involve photopheresis of a fluid. In some embodiments, the activity of cells (e.g., white blood cells) may be affected to reduce an undesired immune response. A need therefore exists to be able to treat fluids, including biological fluids, efficiently and effectively.

Embodiments have been made in light of these and other considerations. However, the relatively specific problems discussed above do not limit the applicability of the embodiments.

SUMMARY

The summary is provided to introduce aspects of some embodiments in a simplified form and is not intended to identify key or essential elements, nor is it intended to limit the embodiments.

Described are embodiments that include methods of treating a fluid. The methods may introduce a first flow of fluid into a flow cell. The first flow of fluid may then be separated into a second flow of fluid and a third flow of fluid. At least one of the second flow of fluid and/or the third flow of fluid may then be reoriented. The reorienting may be accomplished by changing a direction of the flow of fluid. The second flow of fluid may then be recombined with the third flow of fluid to form a fourth flow of fluid. The fourth flow of fluid may then be separated into a fifth flow of fluid and a sixth flow of fluid. At least one of the fifth flow of fluid and/or the sixth flow of fluid may then be reoriented. The reorienting may be accomplished again by changing a direction of the flow of fluid. The reorienting may involve the same or different directional changes as the first reorienting step. The fifth flow of fluid may then be recombined with the sixth flow of fluid to form a seventh flow of fluid. As part of the method, one or more of the first flow of fluid, the second flow of fluid, the third flow of fluid, the fourth flow of fluid, the fifth flow of fluid, the sixth flow of fluid, or seventh flow of fluid may be treated. In embodiments, the reorienting may include changing directions of flow from a first direction to a second direction and may further include changing directions of flow from the second direction to a third direction. The recombining steps may include stacking flows of fluid together or folding flows of fluid together.

In embodiments, the fluid may include a biological fluid, such as blood or one or more components of blood. In addition, the fluid may in embodiments include a photosensitizer. In some embodiments, the treating may include exposing fluid to energy, such as electromagnetic energy. The electromagnetic energy may include light that may have a wavelength in the ultraviolet spectrum. In other embodiments, the light may have a wavelength in the visible light spectrum. The treating may also include exposing fluid to energy from several directions, e.g., top, bottom, sides, etc. In some embodiments, the fluid may maintain laminar flow throughout the method.

Other embodiments may be directed at methods of treating a fluid that include introducing a first flow of fluid into a flow cell that includes at least one surface. The methods may further include separating the first flow of fluid into a second flow of fluid and a third flow of fluid. At least one of the second flow of fluid and/or the third flow of fluid may be reoriented so that a volume of the fluid not previously exposed to the surface becomes exposed to the surface. The volume of fluid may then be treated at the surface. The second flow of fluid may then be recombined with the third flow of fluid to form a fourth flow of fluid. In embodiments, the surface of the flow cell may be an uneven surface. In some embodiments, the methods may further include separating the fourth flow of fluid into a fifth flow of fluid and a sixth flow of fluid. The fifth flow of fluid and/or the sixth flow of fluid may then be reoriented so that a second volume of the fluid is exposed to the surface. This may be followed by recombining the fifth flow of fluid with the sixth flow of fluid to form a seventh flow of fluid.

In embodiments, the fluid may include particles. The particles may include cells or pathogens, in some embodiments. In addition to particles, the fluid may include a photosensitizer. The treating may include in some embodiments exposing the volume to light that may include light with a wavelength in the ultraviolet spectrum and/or the visible light spectrum. In some embodiments, the steps may be performed with the fluid maintaining a laminar flow during the steps of the method.

Other methods may be directed at inactivating a pathogen in a fluid. In embodiments, these methods may include introducing a first flow of fluid into a flow cell that includes a first surface and a second surface. The flow of fluid may be separated into a second flow of fluid and a third flow of fluid. The methods may provide for the second flow of fluid and/or the third flow of fluid to be reoriented so that a first volume of the fluid not previously exposed to the first surface or the second surface becomes exposed to at least one of the first surface or the second surface. The first surface and the second surface may then be exposed to electromagnetic energy, which may inactivate a pathogen in the volume of fluid. The second flow of fluid may then be recombined with the third flow of fluid to form a fourth flow of fluid. In embodiments, the fluid may include blood or one or more components of blood. The fluid may also in embodiments include a photosensitizer. The electromagnetic energy may include light with a wavelength in the ultraviolet spectrum. In other embodiments, the methods may further include separating the fourth flow of fluid into a fifth flow of fluid and a sixth flow of fluid. The fifth flow of fluid and/or the sixth flow of fluid may be reoriented so that a second volume of the fluid is exposed to at least one of the first surface or the second surface. The fifth flow of fluid may then be recombined with the sixth flow of fluid to form a seventh flow of fluid. In some embodiments, the electromagnetic energy may include light with a wavelength of between about 100 nm and about 400 nm. The first flow of fluid may be introduced into the flow cell at a flow rate of between about 1 ml/min to about 1000 ml/min, in some embodiments. Embodiments may provide for the first surface and or the second surface to be exposed to light at an irradiance of between about 1 mW/cm2 and about 300 mW/cm2. In embodiments, fluid may maintain laminar flow during the steps of the method.

Other methods may be directed at affecting cells in a fluid. In embodiments, these methods may include introducing a first flow of fluid into a flow cell that includes a first surface and a second surface. The flow of fluid may be separated into a second flow of fluid and a third flow of fluid. The methods may provide for the second flow of fluid and/or the third flow of fluid to be reoriented so that a first volume of the fluid not previously exposed to the first surface or the second surface becomes exposed to at least one of the first surface or the second surface. The first surface and the second surface may then be exposed to electromagnetic energy, which may affect cells in the volume of fluid. In embodiments, the cells may be white blood cells. The second flow of fluid may then be recombined with the third flow of fluid to form a fourth flow of fluid. In embodiments, the fluid may include blood or one or more components of blood. The fluid may also in embodiments include a photosensitizer. The electromagnetic energy may include light with a wavelength in the ultraviolet spectrum and/or in the visible light spectrum. In other embodiments, the methods may further include separating the fourth flow of fluid into a fifth flow of fluid and a sixth flow of fluid. The fifth flow of fluid and/or the sixth flow of fluid may be reoriented so that a second volume of the fluid is exposed to at least one of the first surface or the second surface. The fifth flow of fluid may then be recombined with the sixth flow of fluid to form a seventh flow of fluid. In some embodiments, the electromagnetic energy may include light with a wavelength of between about 100 nm and about 500 nm. The first flow of fluid may be introduced into the flow cell at a flow rate of between about 1 ml/min to about 1000 ml/min, in some embodiments. Embodiments may provide for the first surface and or the second surface to be exposed to light at an irradiance of between about 1 mW/cm2 and about 300 mW/cm2. In embodiments, fluid may maintain laminar flow during the steps of the method.

Some embodiments are directed to flow cells for treating a fluid. The flow cells may include an inlet port for introducing fluid into the flow cell and at least one manipulation element in fluid communication with the inlet port. The manipulation element may include a channel in fluid communication with the inlet port. A cross-section of the channel may have at least a first dimension. A separation zone may be in fluid communication with the channel and separate a first flow of fluid in the channel into a second flow and a third flow. A reorienting zone may be in fluid communication with the separation zone and may reorient at least one of the second flow or the third flow of fluid. A recombining zone may be in fluid communication with the reorienting zone and may recombine the second and third flows. An outlet port may be in fluid communication with the manipulation element for removing fluid from the flow cell. In embodiments, at least one of the separation zone, the reorienting zone, and the recombining zone may be substantially transmissive to a form of electromagnetic energy (e.g., ultraviolet and/or visible light). The reorienting zone may in embodiments include a first junction that changes a direction of flow of the first flow of fluid from a first direction to a second direction. The first direction may on the same plane as the second direction. The reorienting zone may further include a second junction that may change a direction of flow from the second direction to a third direction, which in embodiments may not be on the same plane as the first direction. Embodiments provide for the flow cell to be made of a polymeric material, which may be either rigid or flexible. The polymeric material may include poly (ethylene-vinyl acetate) (PEVA) and/or 1,2-cyclohexane dicarboxylic acid diisononyl ester (DINCH). The first dimension may in embodiments be greater than about 0.4 mm and may in embodiments be less than about 30 mm. The flow cell may include greater than or equal to about 20 manipulation elements in fluid communication with each other in some embodiments and may include less than or equal to about 5000 manipulation elements in fluid communication with each other in other embodiments.

Other embodiments may be directed to flow cells for manipulating a fluid. The flow cells may include a first channel, a first splitter in fluid communication with the first channel, a second channel in fluid communication with the first splitter and a first elbow, a third channel in fluid communication with the first splitter and a second elbow, a third elbow in fluid communication with the first elbow, a first recombiner in fluid communication with the third elbow and the second elbow, a fourth channel in fluid communication with the first recombiner, a second splitter in fluid communication with the fourth channel, a fifth channel in fluid communication with the second splitter and a fifth elbow, a sixth channel in fluid communication with the second splitter and a sixth elbow, a second recombiner in fluid communication with the fifth elbow and the sixth elbow, and a seventh channel in fluid communication with the second recombiner. In embodiments, at least the first channel, the second channel, the third channel, the fourth channel, the fifth channel, the sixth channel, or the seventh channel may include a first dimension that is between about 0.5 mm and about 5 mm. The flow cells may include a fourth elbow in fluid communication with the second elbow and the first recombiner, in some embodiments. In other embodiments, the flow cells may include a seventh elbow in fluid communication with the fifth elbow and the second recombiner and/or an eighth elbow in fluid communication with the sixth elbow and the second recombiner. The first elbow or the second elbow may be a 90-degree elbow in embodiments. The third elbow, fourth elbow, fifth elbow, sixth elbow, seventh elbow, or eighth elbow may be a 90-degree elbow in other embodiments. The flow cell may be formed by a first sheet of polymeric material being attached to a second sheet of polymeric material, with the first sheet and/or the second sheet being transmissive to light. In some embodiments, the first sheet and the second sheet may be made of a rigid polymeric material or a flexible polymeric material. At least one of the first channel, second channel, third channel, fourth channel, fifth channel, sixth channel, or seventh channel may have a first dimension that is between about 0.6 mm and about 3 mm, between about 0.7 mm and about 2 mm, or between about 0.75 mm and about 1.5 mm.

Some embodiments may be directed at flow cells for treating a fluid that include an inlet port for introducing fluid into the flow cell, a first manipulation element, in fluid communication with the inlet port. The first manipulation element may include a first channel in fluid communication with the inlet port. Embodiments may provide for a cross-section of the first channel having at least a first dimension. The first manipulation element may further include a first separation zone in fluid communication with the first channel. The first manipulation element may include a first separation zone that may separate a first flow of fluid in the channel into a second flow and a third flow of fluid. The first manipulation element may also include a first reorienting zone that may be in fluid communication with the first separation zone and may reorient at least one of the second flow and/or the third flow. The first manipulation element may further include a first recombining zone that may be in fluid communication with the first reorienting zone and that may recombine the second flow of fluid and the third flow of fluid. The flow cell may further include a second manipulation element, wherein the second manipulation element may be in fluid communication with the first manipulation element. The second manipulation element may include a second channel in fluid communication with the first manipulation element. The second manipulation element may include a second separation zone in fluid communication with the second channel. The second separation zone may separate a fourth flow of fluid in the second channel into a fifth flow of fluid and a sixth flow of fluid. The second manipulation element may include a second reorienting zone in fluid communication with the second separation zone. The second reorienting zone may reorient at least one of the fifth flow or the sixth flow and may have a different geometry than the first reorienting zone. The second manipulation element may further include a second recombining zone in fluid communication with the second reorienting zone. The fifth flow of fluid and the sixth flow of fluid may be recombined in the second recombining zone. The flow cell may include several of the first manipulation elements and several of the second manipulation elements. In embodiments, the flow cell may include one of the first manipulation elements followed by one of the second manipulation elements. In other embodiments, the flow cell may include several of the first plurality of manipulation elements followed by several of the second manipulation elements in series.

BRIEF DESCRIPTION OF THE DRAWINGS

Non-limiting and non-exhaustive embodiments are described with reference to the following figures.

FIG. 2E illustrates a view of a flow cell according to embodiments.

FIG. 2F illustrates a view of a flow cell according to embodiments.

FIG. 2G illustrates a cross-sectional view of the flow cell shown in FIG. 2E according to embodiments.

FIG. 2H illustrates a cross-sectional view of the flow cell shown in FIG. 2F according to embodiments.

FIG. 3A-E illustrates embodiments of cross-sections of channels according to embodiments.

FIG. 7A illustrates a top view of an embodiment of manipulation elements.

FIG. 7B illustrates a bottom view of FIG. 7A.

FIG. 8A illustrates a top view of another embodiment of manipulation elements.

FIG. 8B illustrates a bottom view of FIG. 8A.

FIG. 9A illustrates a top view of another embodiment of manipulation elements.

FIG. 9B illustrates a bottom view of FIG. 9A.

DETAILED DESCRIPTION

Figure 1A:
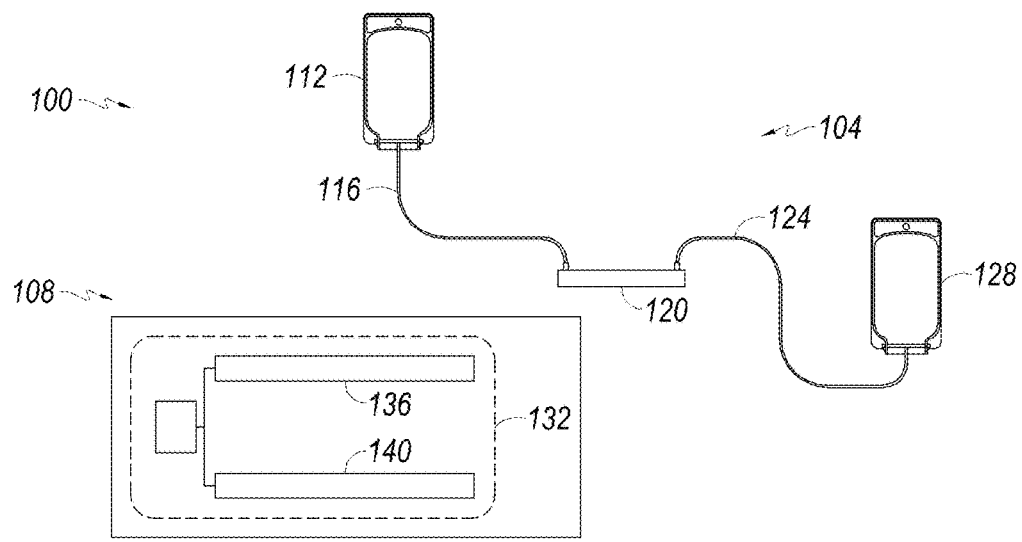
FIG. 1A illustrates a flow-through fluid treatment system according to one embodiment.

The principles of the present invention may be further understood by reference to the following detailed description and the embodiments depicted in the accompanying drawings. It should be understood that although specific features are shown and described below with respect to detailed embodiments, the present invention is not limited to the embodiments described below or shown in the drawings. It is noted that several embodiments are described with respect to treating a fluid to reduce pathogens in whole blood or blood components (e.g., plasma, platelets, red blood cells, leukocytes, buffy coat, or combinations thereof) or to affect cells in a fluid (e.g., leukocytes). However, the present invention is not limited to use with any specific type of fluid or for any particular treatment. Rather, the specific embodiments may be implemented with other fluids including biological fluids, non-biological fluids, or combinations thereof. Additionally, although embodiments below may be described with respect to pathogen reduction or cellular affects, the features of the present disclosure may be used in different fluid treatments.

Reference will now be made in detail to the embodiments illustrated in the accompanying drawings and described below. Wherever possible, the same reference numbers are used in the drawings and the description to refer to the same or similar parts.

FIG. 1A illustrates an embodiment of a system 100 that may be used to treat a fluid. The system 100 may include a flow cell system 104 and a flow cell holder 108. As described in greater detail below, the flow cell system 104 may work with flow cell holder 108 to treat a fluid.

Flow cell system 104 may include a first container (e.g., bag 112) which in embodiments contains the fluid to be treated. Bag 112 may be connected to flow cell 120 with tubing 116. Tubing 116 may create a fluid communication path from the bag 112 to the flow cell 120. Flow cell 120 may be connected to a second container (e.g., bag 128) with tubing 124, which may create a fluid communication path between flow cell 120 and bag 128.

Flow cell holder 108 may include components, systems, or devices that may be used to treat fluid as it flows through flow cell 120. In some embodiments, flow cell system 104 may be implemented as a disposable that may be used to treat a single volume of fluid.

Figure 1B:
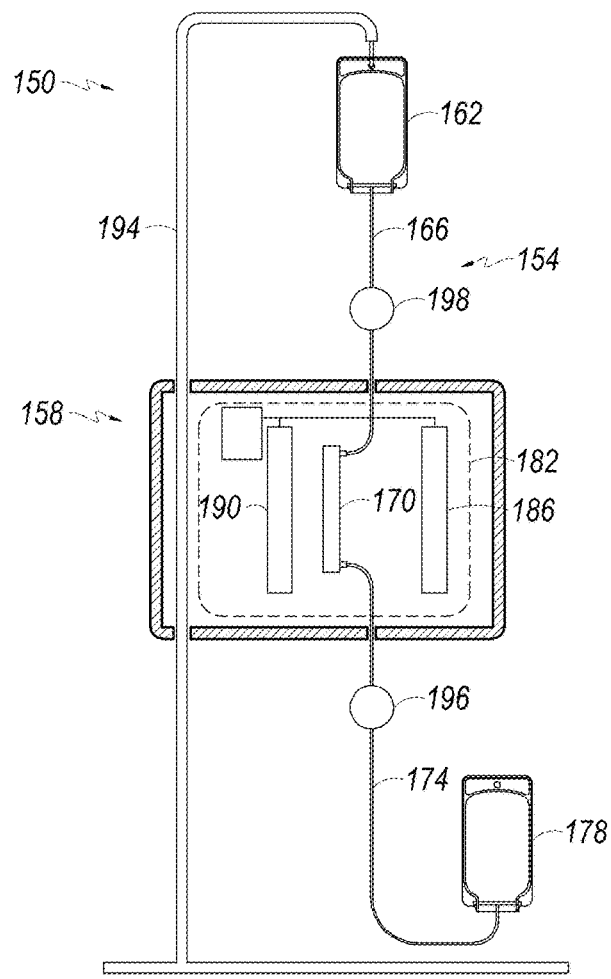
FIG. 1B illustrates a flow-through fluid treatment system according to another embodiment.

FIG. 1B illustrates another flow-through system 150. As shown in FIG. 1B, system 150 illustrates a flow cell system 154 and a flow cell holder 158. Flow cell system 154 may include a first container (e.g., bag 162) which in embodiments may contain the fluid to be treated, for example, a biological fluid, such as blood or a blood component (e.g., red blood cells, plasma, platelets, buffy coat, leukocytes, or combinations thereof). Bag 162 may be connected to flow cell 170 with tubing 166, which may create a fluid communication path from the bag 162 to the flow cell 170. Flow cell 170 is connected to a second container (e.g., bag 178) with tubing 174, which creates a fluid communication path between flow cell 170 and bag 178. As shown in FIG. 1B, flow cell 170 has been positioned in flow cell holder 158. Other embodiments of flow cell systems, and components of flow cells systems may be used in other embodiments.

Systems 100 and 150 may be used in embodiments to treat any type of fluid. The treatment may alter the fluid, or a component of the fluid, as it flows through the flow cells (e.g., 120 and 170). The fluid may be altered by changing a chemical, physical, and/or biological characteristic of the fluid. As non-limiting examples, a treatment may affect cells, viruses, bacteria, proteins, carbohydrates, nucleic acids, or other biological component in a fluid. As other non-limiting examples, a treatment may affect concentration, phases, distribution of components, or other chemical or physical characteristic of a fluid.

As one non-limiting example, flow cells 120 and 170 may be used in treatments such as pathogen reduction of fluids or photopheresis of fluids. In embodiments, the fluids may be biological fluids such as whole blood or fluids that may include one or more components of whole blood. In these example embodiments, the flow cell holders may include illumination systems, e.g., system 132 and system 182. Illumination system 132 may include light sources 136 and 140. Illumination system 182 may include light sources 186 and 190. In embodiments, the light sources may be configured to illuminate flow cells 120 and 170 from at least two directions during a process of treating a fluid, e.g., pathogen reducing a fluid and/or photopheresis.

In other embodiments, flow cells 120 and 170 may be used in other treatments. In these example embodiments, the flow cell holders may include other systems, e.g., system 132 and system 182 may not include light sources, for treating a fluid. Systems that provide energy sources, chemical sources, etc. may be part of system 100 and/or 150.

In embodiments, flow cell holders 108 and 158 may be configured with features to hold flow cells 120 and 170 but allow the flow cells to be removed after a treatment process has been completed. Some non-limiting examples of features include clips, rails, shelves, biased members, springs, sliding members, locks, hooks, etc.

System 150 also includes a stand 194. Stand 194 may include a base and a pole that may be used to hold a source of fluid to be treated. In operation of system 150, a user may begin a treating process (e.g., pathogen reduction and/or photopheresis) by hanging bag 162 from a pole of stand 194. Bag 162 may in embodiments contain a fluid to be treated. For example, the fluid may be whole blood or a blood component (e.g., red blood cells, plasma, platelets, buffy coat, leukocytes, or combinations thereof). As disclosed below, in some embodiments, the fluid may also contain an additional material, e.g., a photosensitizer, that may aid in the treatment of the fluid, e.g., pathogen reduction process and/or photopheresis. In other embodiments, the fluid may not include any additional material. The user may then position flow cell 170 in flow cell holder 158, between light source 186 and light source 190.

The light sources 186 and 190 may be activated to illuminate flow cell 170 from at least two directions. A fluid flow control device 198 may be activated, e.g., opened, to allow fluid to flow from bag 162 into flow cell 170. In embodiments, fluid flow control device 198 may be one or more of a clip, clamp, a frangible, a pump or combinations thereof. In one embodiment, the flow control device 198 may be a pump that when turned on moves fluid from bag 162, through flow cell 170, and into bag 178.

In other embodiments, there may be more than one fluid flow control device, e.g., fluid flow control device 198 which is located in a different location, e.g., such as along tubing 174. In embodiments, fluid flow control device 196 may be a pump that creates pressure in flow cell 170 drawing fluid through the flow cell 170. In other embodiments, the flow control device 196 may be one or more of a clip, clamp, a frangible, a pump, or combinations thereof.

In yet other embodiments, a fluid flow control device may be located on both tubing 166 and tubing 174 (e.g., 196 and 198). A user may activate both fluid flow control devices to allow fluid to flow from bag 162 into flow cell 170. In some embodiments, the fluid flow control devices 196 and 198 may be activated individually, e.g., 196 ON and 198 OFF; or 196 OFF and 198 ON.

As the fluid flows through the flow cell 170, the fluid may be illuminated by light sources 186 and 190 causing the fluid to be treated, e.g., a reduction in pathogens or photopheresis. After treatment, the fluid may flow from flow cell 170 into bag 178 for storage.

In embodiments, the light sources 186 and 190 may radiate light of a particular wavelength that treats the fluid, e.g., a pathogen reducing effect or a photopheresis effect. For example, light sources 186 and 190 may radiate light in the ultraviolet spectrum such as light with a wavelength of between about 100 nm and about 400 nm. In other embodiments, the light sources may radiate light in the visible light spectrum such as between about 300 nm and about 800 nm. In yet other embodiments, the light sources may radiate light in a combination of ultraviolet and visible light spectrums, for example with wavelengths of between about 100 nm and about 500 nm. Some embodiments provide for use of light sources that radiate ultraviolet light within more specific ranges. As some non-limiting examples, some embodiments may utilize light sources that radiate UVA (wavelengths from about 315 nm to about 400 nm), UVB (wavelengths from about 280 nm to about 315 nm) and/or UVC (wavelengths from about 100 nm to about 280 nm). Other embodiments provide for use of light sources that radiate light with wavelengths from about 10 nm to about 450 nm. Without being bound by theory, it is believed that the energy from the ultraviolet light may destroy nucleic acids and disrupt DNA, which may interfere with cellular processes of microorganisms. As a result, pathogens, such as, but not limited to, viruses and bacteria may be inactivated. Ultraviolet light is merely one example. Other non-limiting examples of possible wavelengths of light that may be used include, visible light such as violet light (wavelengths from about 400 nm to about 420 nm), indigo light (wavelengths from about 420 nm to about 440 nm), blue light (wavelengths from about 440 nm to about 490 nm), green light (wavelengths from about 490 nm to about 570 nm), yellow light (wavelengths from about 565 nm to about 590 nm), orange light (wavelengths from about 590 nm to about 625 nm), red light (wavelengths from about 625 nm to about 740 nm). In embodiments, light sources 186 and/or 190 may radiate light in any of the ranges noted above or in any combination of the ranges listed above. Light sources 186 and/or 190 may in embodiments be any source of light, some non-limiting examples including incandescent, fluorescent, halogen, LEDs, and combinations thereof.

In other embodiments, in addition to light, the fluid may contain an additional material, e.g., a photosensitizer that aids in the treatment process (e.g., pathogen reduction and/or photopheresis). Without being bound by theory, it is believed that photosensitizers include molecules that may be activated by light energy (e.g., ultraviolet light or visible light). The photosensitizer (or reaction products resulting from the activation) may disrupt bonds in DNA. In pathogens, such as, but not limited to, viruses and bacteria, the disruption may lead to the death of the pathogen, an inability to reproduce, or otherwise inactivation. In other embodiments, the process may affect cellular components (e.g., white blood cells) in the fluid. In photopheresis, the light energy (e.g., ultraviolet light or visible light) may activate a photosensitizer and may cause cross linkage of DNA which may effectively reduce the activity of the white blood cells to reduce an undesired immune response. Some non-limiting examples of photosensitizers that may be used in some embodiments include: porphyrins, flavins (e.g., riboflavin), psoralens (e.g., 8-methoxypsoralen), acridine, toluidines, phenothiazine derivatives, dyes (e.g., natural red, methylene blue, etc.) and combinations thereof.

Figure 2A:
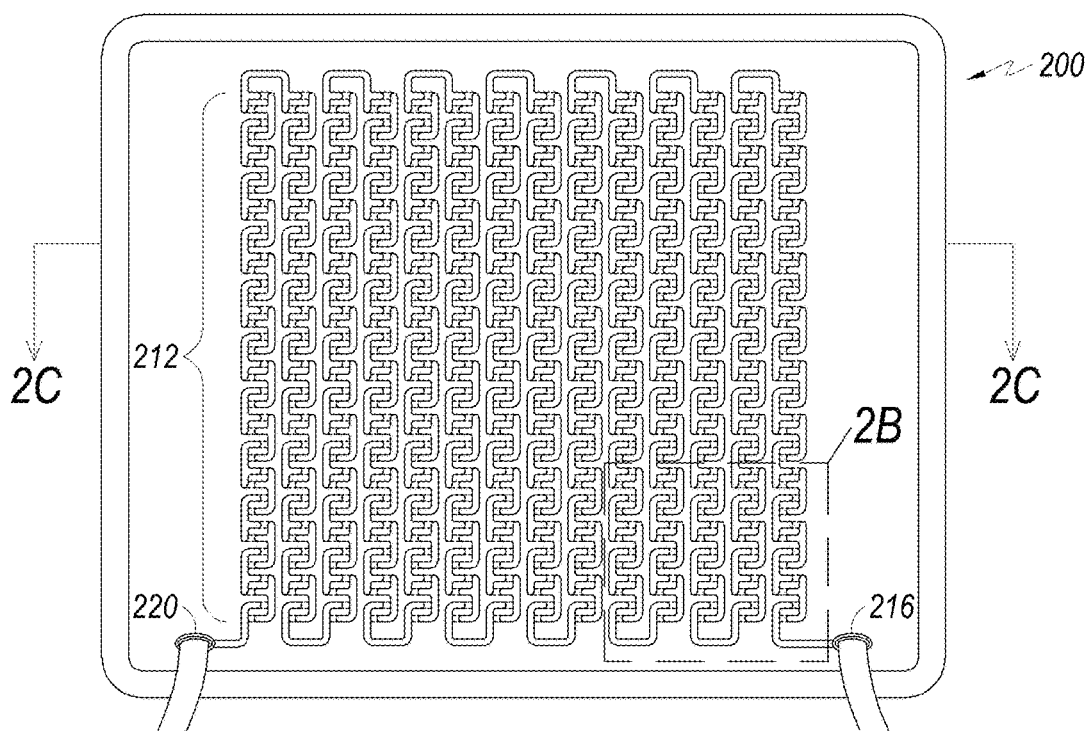
FIG. 2A-C illustrates views of a flow cell according to embodiments.
Figure 2B:
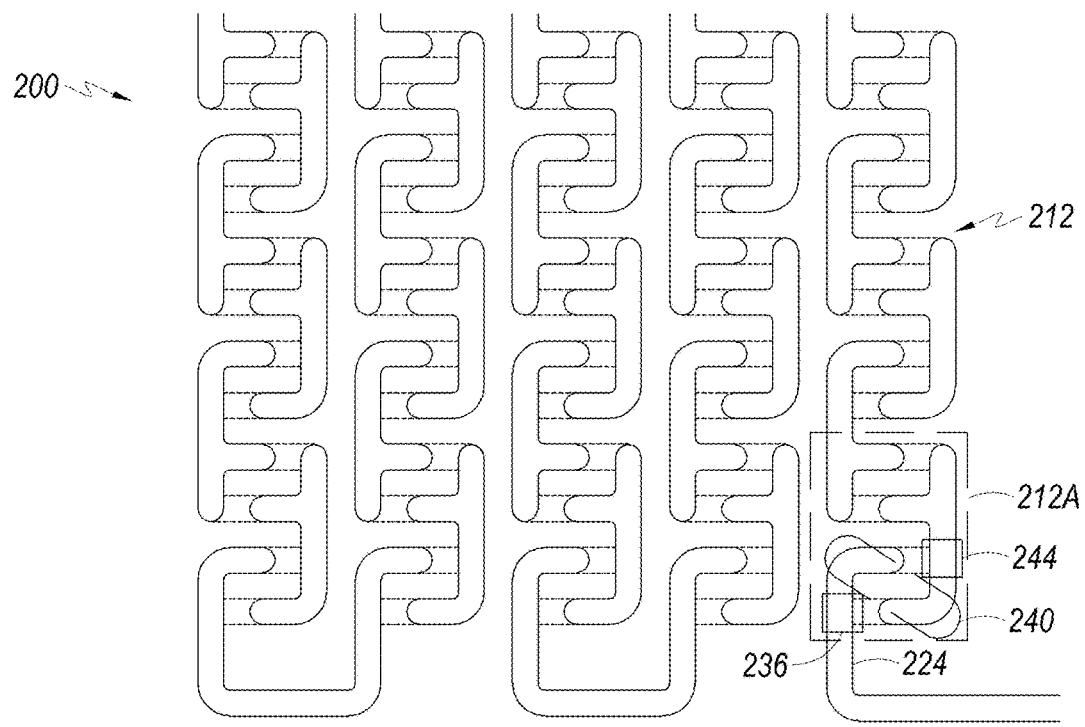
Figure 2C:
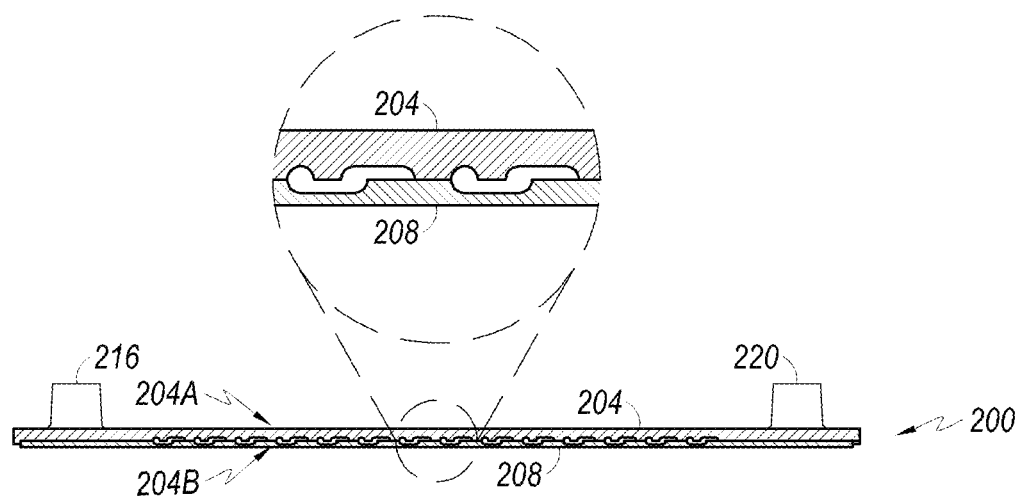
Figure 2D:
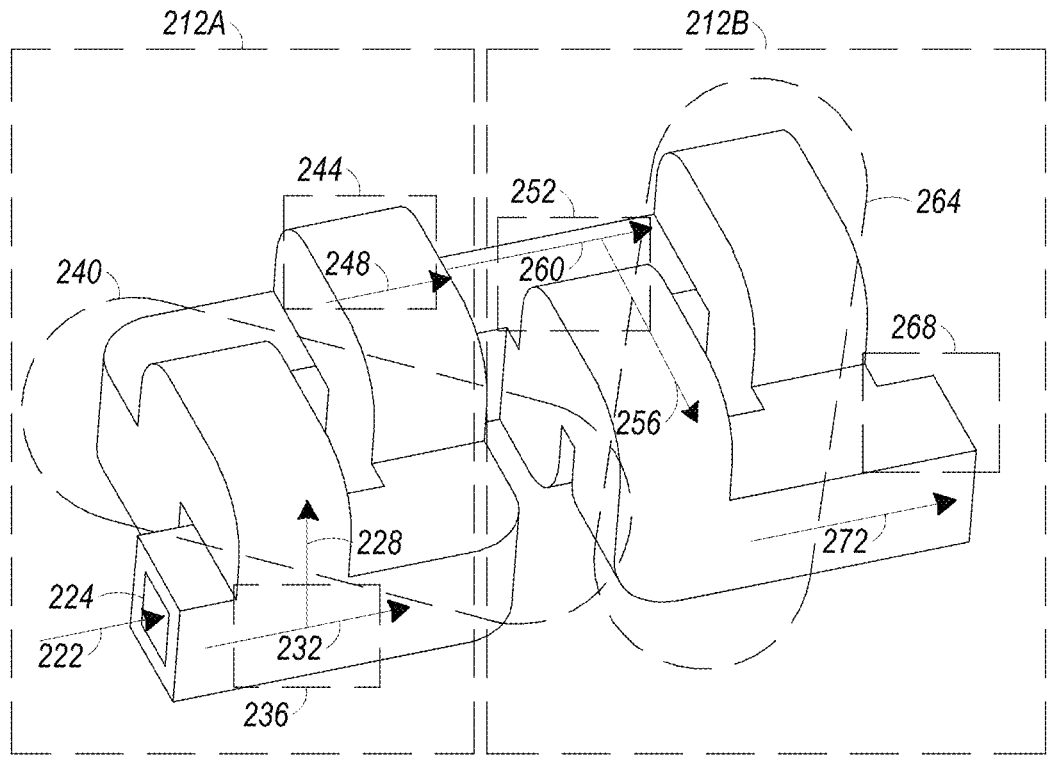
FIG. 2D illustrates a view of fluid flow through one embodiment of manipulation elements.

FIGS. 2A-C illustrate views of a flow cell 200 according to some embodiments. FIG. 2D illustrates flows within a flow cell such as flow cell 200 according to embodiments (from a backside of flow cell 200 compared to FIGS. 2A and 2B). FIGS. 2E and 2F show other flow cells 350 and 370 according to embodiments. FIGS. 2G and 2H illustrate cross-sectional views of flow cells 350 and 370 respectively. The flow cells (e.g., 200, 350, 370, 400, etc.) in the figures and described herein provide examples of flow cells (with manipulation elements) that may be used in some embodiments, in fluid treat systems. For example, in some embodiments, flow cells (e.g., 200, 350, 370, 400, etc.) may be used as flow cells 120 and/or 170 in systems 100 and/or 150 described above.

Embodiments may provide for flow cells 200, 350, and 370 to be made from a first piece (e.g., sheet) and a second piece (e.g., sheet) of material. Generally, flow cells 200, 350, and 370 may include a plurality of manipulation elements (212, 352, and 372), an inlet port (216, 354, and 374) and an outlet port (220, 356, and 376). As described in greater detail below, manipulation elements (212, 352, and 372) may manipulate fluid as it flows through the flow cell (200, 350, and 370) as part of treating the fluid. In embodiments, the manipulation may provide for substantially all of the fluid to be exposed to a surface of a flow cell (200, 350 and/or 370). The surface of the flow cells may in embodiments be flat e.g., surfaces 204A and 208A. In other embodiments, the surface may be uneven due to the structural features of the manipulation elements, e.g., channels, elbows, etc., such as surfaces 353A, 355A, 373A, and 375A. In other embodiments, the manipulation may have a mixing effect on the fluid. In yet other embodiments, the manipulation may distribute different components within a fluid or provide intimate contact between components of a fluid.

Described below is an embodiment of a general process of utilizing a flow cell to treat a fluid. It is noted that the description is provided for illustrative purposes only. Different steps may be used in embodiments of different processes that may utilize flow cell 200, flow cell 350, flow cell 370, flow cell 400, or other embodiments of a flow cell.

Generally, in operation, a fluid to be treated, may be introduced into flow cell, e.g., 200 through inlet port 216. A first flow 222 of fluid may flow from inlet port 216 into a channel 224 that is part of a first manipulation element 212A (FIG. 2B and 2D). The first flow of fluid 222 may be separated into a second flow 228 of fluid and a third flow 232 of fluid at a separation zone 236 that is in fluid communication with channel 224 (FIG. 2B and 2D). The second flow 228 and/or the third flow 232 may move into a reorienting zone 240 (in fluid communication with the separation zone 236) where one or both, of the second flow 228 and the third flow 232, may be reoriented. The second flow 228 and the third flow 232 may then move into a recombining zone 244 (in fluid communication with the reorienting zone 240), where the flows are recombined into a fourth flow 248. As illustrated in FIGS. 2A and 2B, flow cell 200 may include a number of manipulation elements in fluid communication (e.g., in series) that include additional channels, separation zones, reorienting zones, and recombining zones. The manipulation elements may in embodiments be similar in geometries, while in other embodiments, the manipulation elements may have different geometries that perform the separation, reorienting, and recombining. For example, FIGS. 7A-15B illustrate alterative embodiments of manipulation elements that may be used in other embodiments. In embodiments, the separating, reorienting, and recombining may ensure that substantially all of the fluid introduced into the flow cell flows at or near a surface of the flow cell (e.g., surface 204A or 208A of flow cell 200) for some time period, while the fluid is flowing through the flow cell. Finally, the fluid flows out of flow cell 200 through outlet port 220.

In some embodiments, the fluid may be exposed to electromagnetic energy, e.g., light energy, throughout the process of flowing through flow cell 200 as part of treating the fluid. The features of some embodiments of flow cell 200 provide for exposing fluid to light energy (and in some embodiments to a photosensitive material), which reduces pathogens in the fluid and/or affects cells in the fluid. In embodiments, a surface of a flow cell (and consequently fluid exposed to the surface) may be exposed to light at an irradiance of between about 0.5 mW/cm2 and about 100 mW/cm2. As may be appreciated, the irradiance used during a fluid treatment process may depend on other parameters such as flow rate, volume, time of exposure, opacity of the fluid to the energy (e.g., light) etc. In embodiments, the surface of a flow cell may be exposed to light at an irradiance of between about 1.0 mW/cm2 to about 500 mW/cm2, between about 2 mW/cm2 to about 400 mW/cm2, between about 3 mW/cm2 to about 300 mW/cm2, between about 4 mW/cm2 to about 200 mW/cm2, or even between about 5 mW/cm2 to about 100 mW/cm2. In other embodiments, the surface of a flow cell may be exposed to light at an irradiance of between about 1.0 mW/cm2 to about 50 mW/cm2, between about 1.5 mW/cm2 to about 25 mW/cm2, between about 2 mW/cm2 to about 20 mW/cm2, between about 2.5 mW/cm2 to about 15 mW/cm2, or even between about 3 mW/cm2 to about 10 mW/cm2.

In embodiments, flow cell 200 may be designed to ensure that fluid processed through flow cell 200 has a threshold amount of exposure to light energy to reduce pathogens or affect cells in the fluid by a predetermined amount. In other words, the fluid may be provided with a minimum dose of light energy. In those embodiments where pathogens are being reduced, treating the fluid may result in a log reduction of about 1, about 1.5, about 2, about 2.5, about 3, about 3.5, about 4, about 4.5, about 5, about 5.5, about 6.0, about 6.5, about 7.0, about 7.5, about 8.0, about 8.5, about 9.0, about 9.5, or even about 10.

Also, embodiments may be designed to avoid exceeding a maximum threshold amount of exposure to light energy. That is, if the fluid is exposed to an amount of light energy above a threshold amount, other components of the fluid may be negatively affected. For example, too much energy may denature proteins that are desired to be maintained in the fluid. In embodiments, the presence of the manipulation elements 212 may continuously separate, reorient, and recombine the fluid, which may prevent any portion from overexposure to light energy.

Figure 2I:
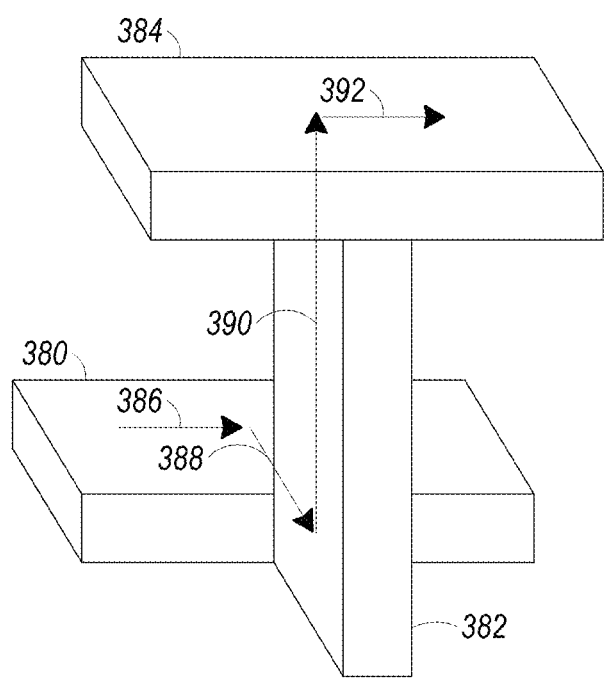
FIG. 2I illustrates various planes and directions.

It is noted that although specific structural features are shown as part of manipulation elements 212 (e.g., 212A and 212B), embodiments are not limited thereto. For example, as shown in FIG. 2D, separation zone 236 of manipulation element 212A may comprise a splitter which separates the first flow of fluid 222 into a second flow 228 and third flow 232. In manipulation element 212A, the splitter separates the first flow of fluid 224, so that the second flow 228 moves in a different direction (e.g., toward a second plane from a first plane) and the third flow 232 continues to move along the same plane. FIG. 2I illustrates a number of planes 380, 382, and 384 and a number of directions 386, 388, 390, and 392. FIG. 2I is provided to show some directions and planes that may illustrate movement of fluid performed by different portions of manipulation elements according to some embodiments. As shown in FIG. 2I, direction 386 is on plane 380. Consistent with some embodiments, a splitter may split a flow so that a portion of the flow (e.g., a second flow) moves in direction 386 and the other portion of the flow (e.g., a third flow) moves in direction 388, which may still be on plane 380. Similarly, a reorientation zone may change a direction of fluid flow from direction 386 to direction 388. In other embodiments, a splitter may split a flow so that a portion of the flow (e.g., a second flow) moves in direction 388 and the other portion of the flow (e.g., a third flow) moves in direction 390, which may be on plane 382. Similarly, a reorientation zone may change a direction of fluid flow from direction 388 to direction 390. In yet other embodiments, a splitter may split a flow so that a portion of the flow (a second flow) moves in direction 390 and the other portion of the flow (a third flow) moves in direction 392, which may be on plane 384. Similarly, a reorientation zone may change a direction of fluid flow from direction 390 to direction 392. It is noted that in some embodiments, a reorientation zone may change a flow of fluid in several directions. For example, a reorientation zone may first change a flow of fluid from direction 386 to direction 388 (on plane 380), followed by a change in direction to direction 390 (on plane 382), followed again by a change in direction to direction 392 on plane 384. These are merely some examples and the embodiments described herein are not limited to splitting fluid, or reorienting fluid, in any specific direction(s).

Referring to FIG. 2D, separation zone 252 of manipulation element 212B includes a splitter which separates a fourth flow 248 (e.g., combination of second 228 and third 232 flows) into a fifth flow 256 and a sixth flow 260. The splitter in separation zone 252 may separate the fourth flow of fluid, so that a fifth flow 256 moves in a direction perpendicular to the sixth flow 260, which may be on the same plane.

With respect to reorienting zones, manipulation element 212A includes reorienting zone 240 with several elbows that reorient flow 228 a number of times, i.e., changes the direction of flow 228. With respect to the view shown in FIG. 2D, an elbow may reorient flow 228 to a different plane than flow 222. Other elbows may change the direction of flow 228 back to the same plane as a plane on which flow 222 initially flows. Flow 228 may then be reoriented 90 degrees on the same plane toward recombining zone 244 by another elbow. The reorienting zone 240 may additionally include an elbow that reorients third flow 232 90 degrees toward recombining zone 244. Additional elbows may then reorient third flow 232 up to a different plane. The third flow 232 may then be stacked with second flow 228 in recombining zone 244.

Manipulation element 212B may include reorienting zone 264 that includes additional elbows that reorient fifth flow 256 up to a different plane than the initial plane of flow 248, then back to the initial plane, and finally, 90 degrees) toward recombining zone 268. The reorienting zone 264 may further include elbows that reorient sixth flow 260 to a different plane and 90 degrees toward recombining zone 268. The reorienting zone 264 may further include elbow(s) that reorient sixth flow 260 back to an initial plane. The fifth flow 256 may then be recombined (e.g., folded) with sixth flow 260 at recombining zone 268 to form a seventh flow 272.

It is noted that the elbows (described above with respect to FIG. 2D and below with respect to FIG. 10A) may have different angles. In some embodiments, the elbows may be 90-degree elbows. In other embodiments, the elbows may be of some other degree (e.g., 10-degree, 20-degree, 30-degree, 45-degree elbows). Therefore, the term "elbow" herein refers to a structure that changes a direction of a flow of fluid. The change in direction may be on the same plane or a different plane as an initial direction.

Flow cell 200 may include, in embodiments, one or more channels that may be part of manipulation elements 212. As described above, channel 224 may be fluidly associated with separation zone 228. Separation zones 228, 252; reorienting zones 240, 264; and/or recombining zones 244, 268 may also include channels as conduits for flows of fluid.

Embodiments are not limited to the particular structural features described above. In other embodiments, for example, separation zones 228, 252 may include different splitters, e.g., other 3-way splitters (e.g., T-junction, Y-junction, etc.), that may separate fluid flows 224, 248. Moreover, the reorienting zones 240, 264 may comprise other combinations of steps, elbows, splitters, junctions, channels, or other features that reorient one or more of the flows of fluid in different directions, either vertically, horizontally, at some other angle (e.g., from 0 degrees to 180 degrees) with respect to vertical or horizontal, a same plane, and/or a different plane. Also, in embodiments, the recombining zones 244, 268 may also have different structural features, e.g., combinations of steps, elbows, splitters, junctions, channels, or other features for recombining fluid flows. These are merely more examples of structural features of manipulation elements, and embodiments are not limited to any specific type(s) of manipulation element geometries.

As some examples of other embodiments, FIGS. 7A-15B illustrate views of fluid flow that utilize different manipulation element geometries. As illustrated in FIGS. 7A-15B, any combination of steps, elbows, splitters, junctions, channels, or other features that separate, reorient, and/or recombine fluid flows may be used with embodiments of the present disclosure.

Figure 10:
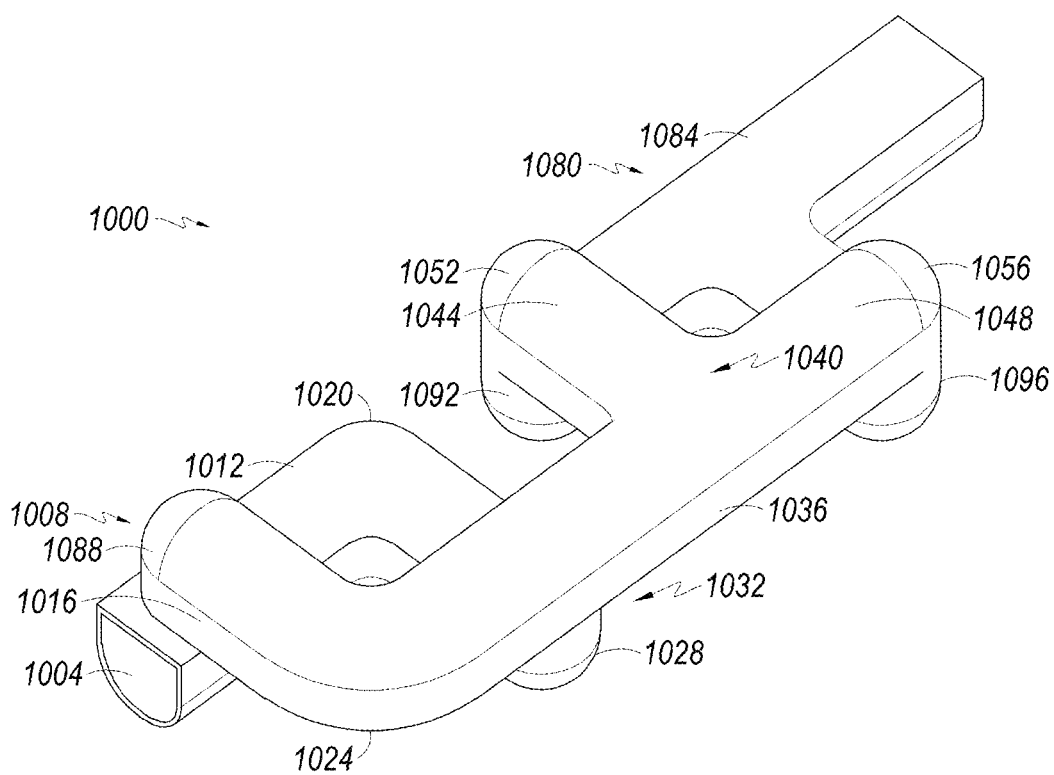
FIG. 10 illustrates a view of another embodiment of manipulation elements.
Figure 11:
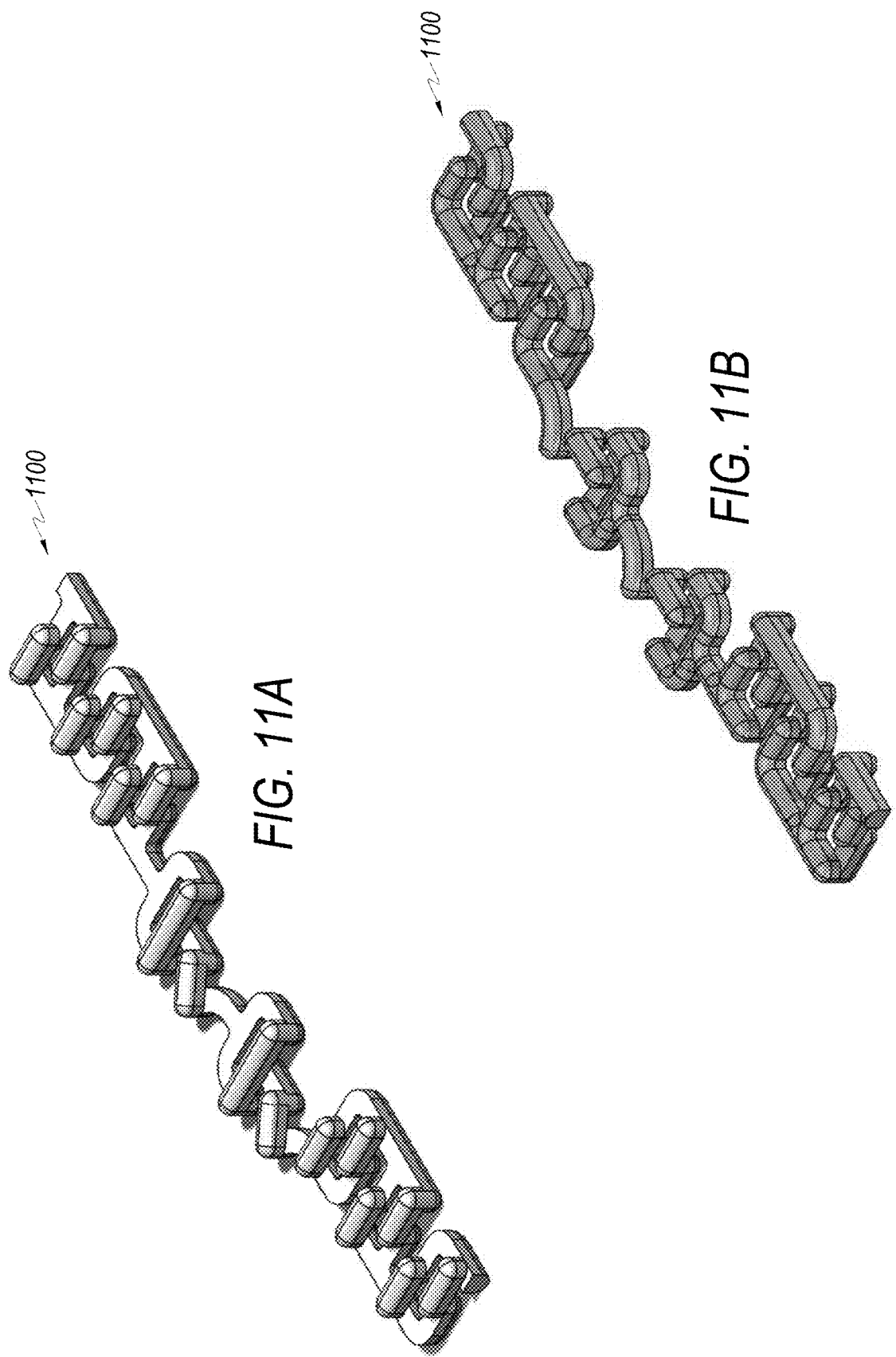
FIG. 11A illustrates a top view of another embodiment of manipulation elements.
FIG. 11B illustrates a bottom view of FIG. 11A.
Figure 12:
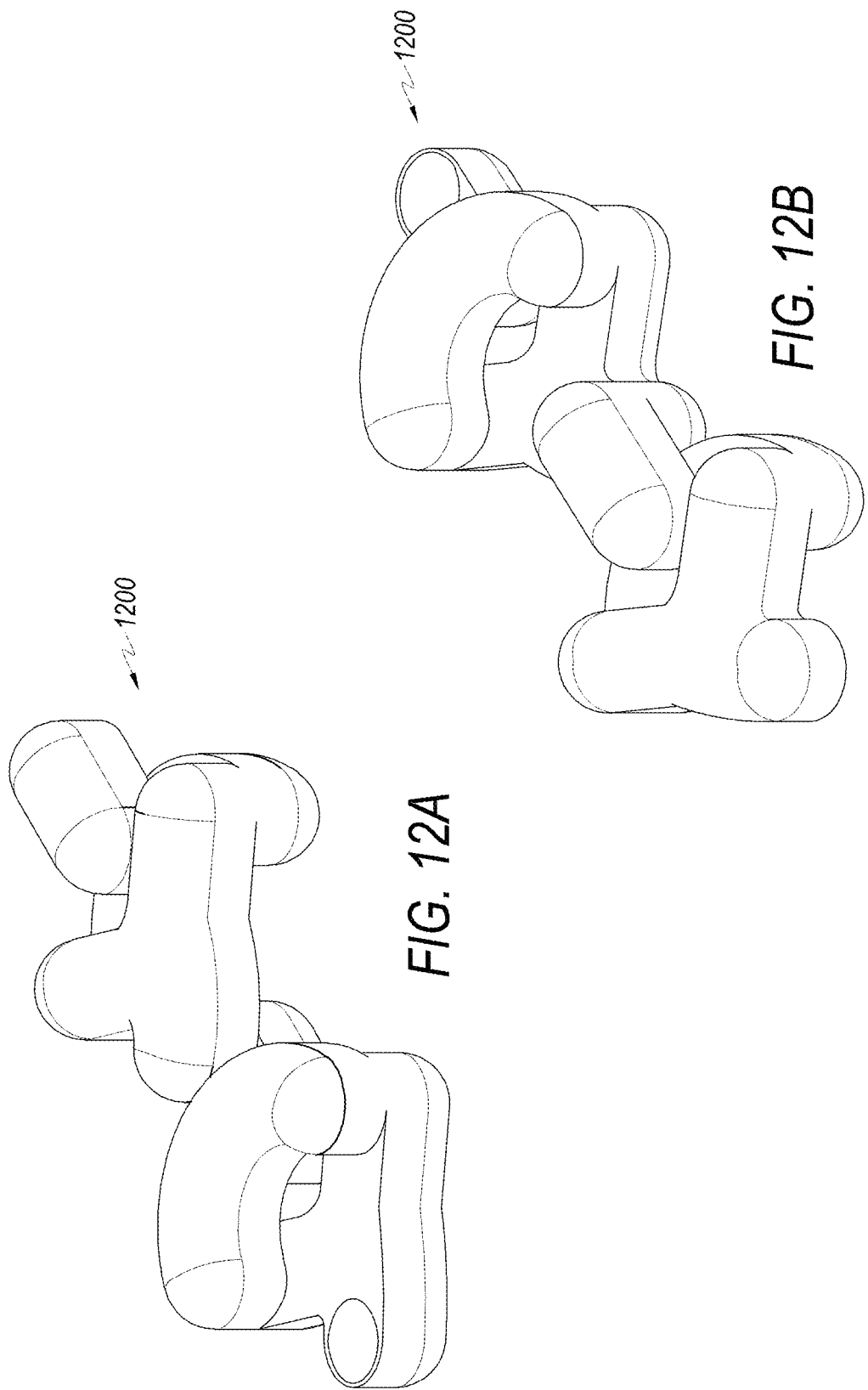
FIG. 12A illustrates a top view of another embodiment of manipulation elements.
FIG. 12B illustrates a bottom view of FIG. 12A.
Figure 13:
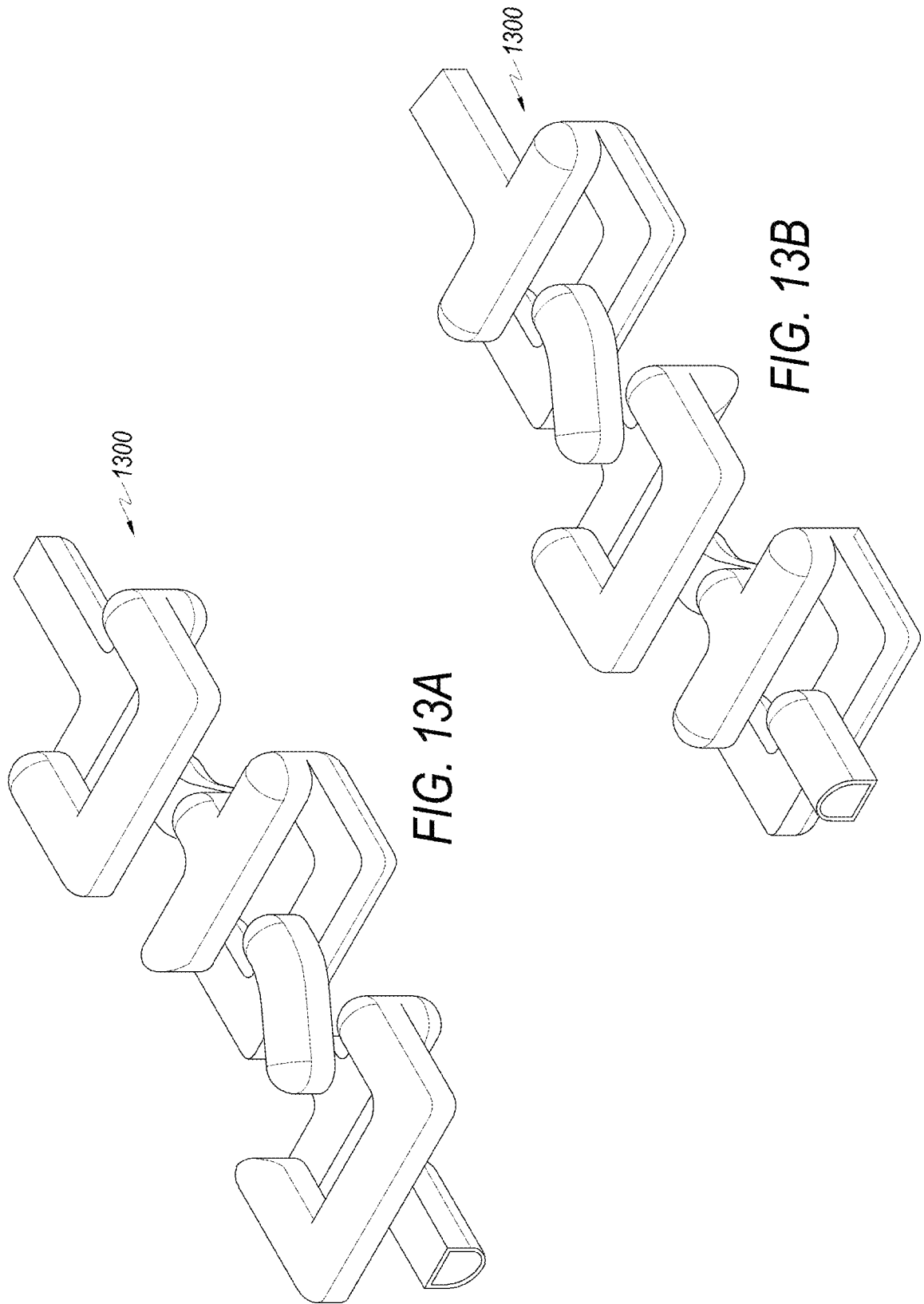
FIG. 13A illustrates a top view of another embodiment of manipulation elements.
FIG. 13B illustrates a bottom view of FIG. 13A.
Figure 14:
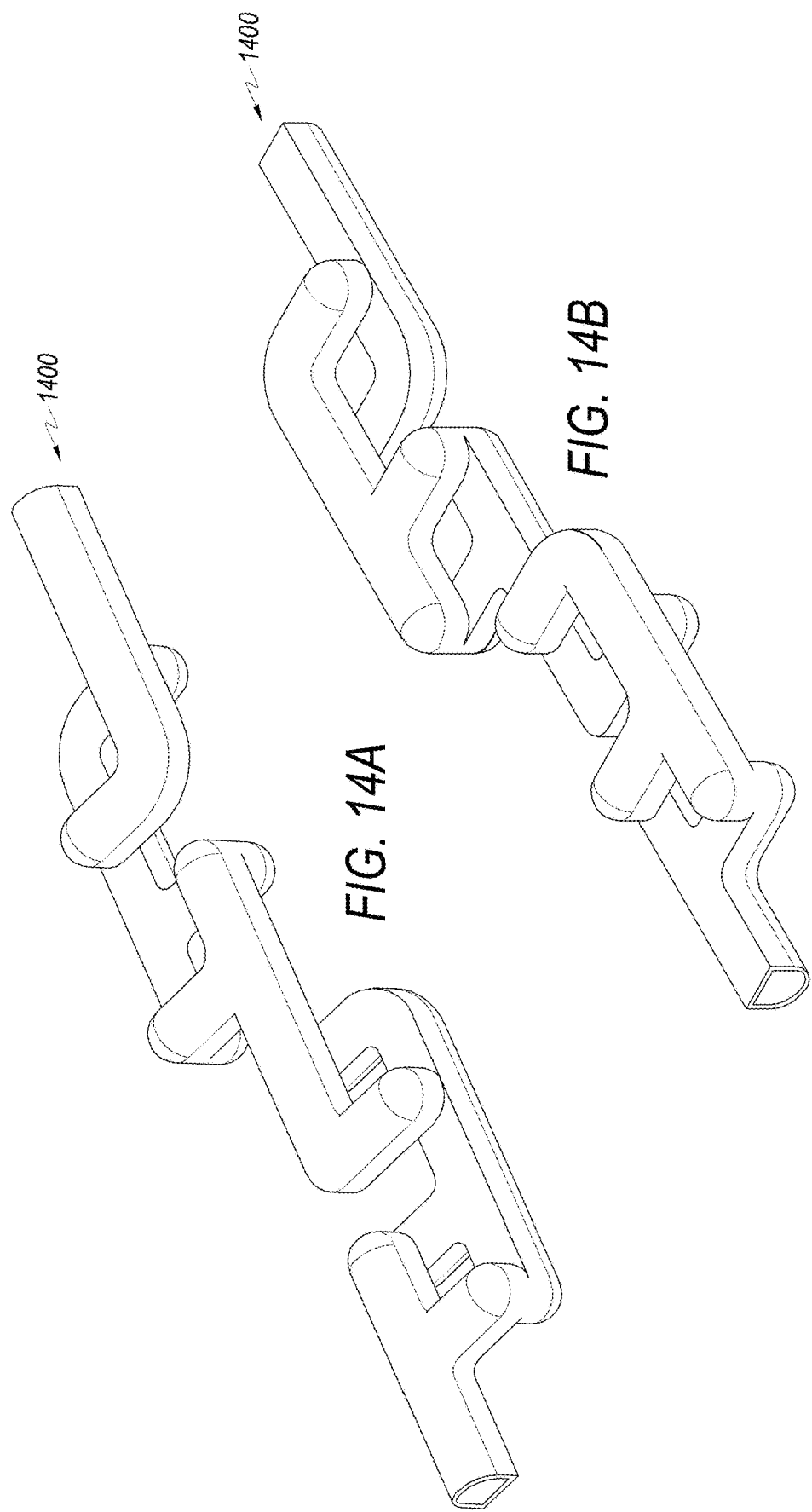
FIG. 14A illustrates a top view of another embodiment of manipulation elements.
FIG. 14B illustrates a bottom view of FIG. 14A.
Figure 15:
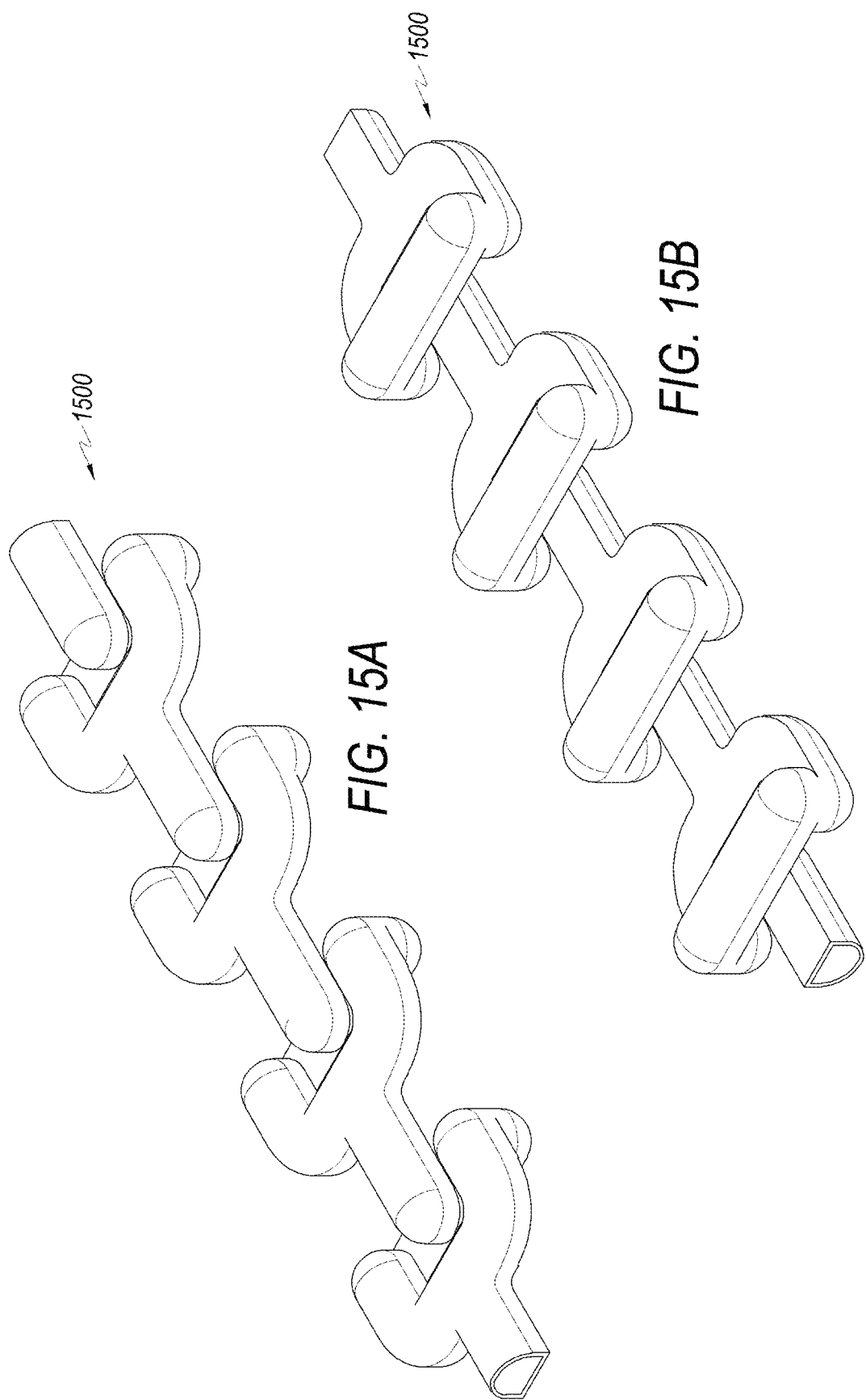
FIG. 15A illustrates a top view of another embodiment of manipulation elements.
FIG. 15B illustrates a bottom view of FIG. 15A.

For example, FIG. 10A illustrates an embodiment of manipulation element(s) 1000 implemented by various structures. Manipulation element 1000 may be part of a flow cell that may include a number of similar manipulation elements or manipulation elements of different geometries. The description below is provided merely for explanatory purposes, and as illustrated in FIGS. 7A-15B, embodiments may provide for various combinations of channels, elbows, etc. to implement portions of manipulation elements.

Element 1000 includes a first channel 1004. First channel 1004 may be in fluid communication with for example an inlet port of a flow cell. Fluid may enter a flow cell through the inlet port and flow through channel 1004. A first splitter 1008 may be in fluid communication with the first channel and split the flow of fluid. A second channel 1012 may be in fluid communication with first splitter 1008 and provide a conduit for a second flow of fluid split from the first flow of fluid. A third channel 1016 may be in fluid communication with the splitter 1008 and provide a conduit for a third flow of fluid split from the first flow of fluid. The second channel 1012 may be in fluid communication with a first elbow 1020. The third channel 1016 may be in fluid communication with the splitter 1008 and a second elbow 1024. A third elbow 1028 may be in fluid communication with the first elbow 1020.

Element 1000 may also include a first recombiner 1032 in fluid communication with the second elbow 1024 and the third elbow 1028. The first recombiner 1032 recombines the second flow of fluid and the third flow of fluid that were separated by the first separator 1008. A fourth channel 1036 is in fluid communication with the first recombiner 1032 and provides a conduit for a fourth flow (e.g., combination of second and third flows). The fourth channel 1036 is in fluid communication with a second splitter 1040. The second splitter 1040 may split the flow of fluid again. A fifth channel 1044 may be in fluid communication with second splitter 1040 and provide a conduit for a fifth flow of fluid split from the fourth flow of fluid. A sixth channel 1048 may be in fluid communication with the splitter 1040 and provide a conduit for a sixth flow of fluid split from the fourth flow of fluid. The fifth channel 1044 may be in fluid communication with a fifth elbow 1052. The sixth channel 1048 may be in fluid communication with the splitter 1040 and a sixth elbow 1056. A second recombiner 1080 may be in fluid communication with the fifth elbow 1052 and the sixth elbow 1056. The second recombiner 1080 may recombine the fifth flow of fluid and the sixth flow of fluid that were separated by the second separator 1040. A seventh channel 1084 is in fluid communication with the second recombiner 1080 and provides a conduit for a seventh flow of fluid (e.g., combination of fifth and sixth flows).

It is noted that although specific features of the manipulation elements are described, the present embodiments are not limited to such features. For example, as noted above, the second elbow 1024 may be in fluid communication with the first splitter 1008. However, between the first splitter 1008 and the second elbow 1024 there may be other features. For example, a fourth elbow 1088 is positioned between splitter 1008 and elbow 1024. As another example, a seventh elbow 1092 may be positioned between the fifth elbow 1052 and the second recombiner 1080. An eight elbow 1096 may be positioned between the sixth elbow 1056 and the second recombiner 1080. These are merely some examples. In other embodiments, there may be additional features positioned between two features that still allow for fluid communication between the two features.

As previously noted, the elbows described above (e.g., with respect to FIG. 2D and below with respect to FIG. 10A) may have different angles. In some embodiments, the elbows may be 90-degree elbows. In other embodiments, the elbows may be of some other degree (e.g., 10-degree, 20-degree, 30-degree, 45-degree elbows). The term "elbow" herein is intended therefore to refer to a structure that changes a direction of a flow of fluid. The change in direction may be on the same plane or to a plane that is different from a plane of an initial direction.

The different geometries of manipulation elements illustrated in FIGS. 2A-2H and 7A-15B, provide for thorough manipulation of fluids. Without being bound by theory, it is believed that embodiments of the manipulation elements provide for ordered (e.g., laminar) manipulation. Separating, reorienting, and recombining fluid flows (with the manipulation elements) is believed to expose substantially all of the fluid to the surface. In other words, the manipulation elements ensure that substantially all of the fluid, as it flows through a flow cell, will travel to the surface for some period of time to ensure the fluid is treated (e.g., exposed to energy (such as illuminated, heated, etc.) component added, component removed, etc.). In some embodiments, the separating, reorienting, and recombining fluid flows may also have the effect of mixing the fluid. In other embodiments, the treatment may provide for distributing components throughout a fluid and/or bringing components of a fluid into intimate contact.

Additionally, embodiments of some flow cells may include other features not described above. As one non-limiting example, there may be information taken by sensors at various locations in the flow cell. For example, sensing fluid flow, transmissivity of the fluid, fluid movement, etc. may be performed at various locations in the flow cell. In some embodiments, the flow cell may include some locations with different characteristics (e.g., windows) that facilitate sensors obtaining fluid information.

Referring to FIGS. 3A-3E, various embodiments are shown of cross-sections of channels that may correspond to channels in embodiments of a flow cell (e.g., channels 224, 1004, 1012, 1036, 1044, 1048, 1084, etc.). For example, FIG. 3A illustrates a rectangular cross-section 300 that includes a height 304 and a width 308. FIG. 3B illustrates an elliptical cross-section 312 that includes a minor axis length 316 and a major axis length 320. FIG. 3C illustrates a circular cross-section 324 with a diameter 328. FIG. 3D illustrates a semi-circular cross-section 330 with a width 332 and a radius 334. FIG. 3E illustrates a semi-elliptical cross-section 336 with a width 338 and a radius 340. FIGS. 3A-3E are provided merely for illustrative purposes. In embodiments, cross-sections may have different shapes curves, arcs, lines, angles, or combinations thereof.

In embodiments, one or more of the channels may have particular dimensions. In some embodiments, dimension(s) of the channels may be selected to optimize/control factors such as: treatment time, flow rate(s), volume, pressure, shear rates, etc. In embodiments where the fluid may include cells, having relatively small channels may increase the pressure and shear rate experienced by the fluid when flowing through the flow cell. The increased pressure and shear rate may affect the fluid negatively. For example, if the fluid includes whole blood or blood components, the increase in pressure and shear rate may for example activate platelets (causing coagulation) and/or lyse red blood cells. Also, it may be difficult to manufacture flow cells that include channels that have small dimensions. Accordingly, in these embodiments, the dimensions of a channel's cross-section may be selected to avoid at least some of these effects.

In one embodiment, a channel(s) may have at least one dimension that is greater than about 0.3 mm. For example, if the channel has a rectangular cross-section, at least a height 304 or a width 308 may be greater than about 0.3 mm. If the channel(s) has an elliptical cross-section, at least a minor axis 316 or a major axis 320 may be greater than about 0.3 mm. If the channel(s) has a circular cross-section, at least a diameter 328 may be greater than about 0.3 mm. If the channel(s) has a semi-circular cross-section, at least a width 332 or a radius 334 may be greater than about 0.3 mm. If the channel(s) has a semi-elliptical cross-section, at least a width 338 or a radius 340 may be greater than about 0.3 mm. In other embodiments, channel(s) may have at least one dimension that is greater than or equal to about 0.4 mm, greater than or equal to about 0.5 mm, greater than or equal to about 0.6 mm, greater than or equal to about 0.7 mm, greater than or equal to about 0.8 mm, greater than or equal to about 0.9 mm, greater than or equal to about 1.0 mm, greater than or equal to about 1.1 mm, greater than or equal to about 1.2 mm, greater than or equal to about 1.3 mm, greater than or equal to about 1.4 mm, or even greater than or equal to about 1.5 mm.

In some embodiments, having relatively large channels may also pose some challenges. In some embodiments, the fluid may require a minimum period of time for treatment. As a result, if the channels in a flow cell are too large the fluid may require more manipulation, because the larger dimensions may not allow fluid to be manipulated as well. In these embodiments, the dimensions of a channel's cross-section may be selected to avoid these effects.

In one embodiment, a channel(s) may have at least one dimension that is less than about 30 mm. For example, if the channel(s) has a rectangular cross-section, at least a height 304 or a width 308 may be less than about 30 mm. If the channel(s) has an elliptical cross-section, at least a minor axis 316 or a major axis 320 may be less than about 30 mm. If the channel(s) has a circular cross-section, at least a diameter 328 may be less than about 30 mm. If the channel(s) has a semi-circular cross-section, at least a width 332 or a radius 334 may be less than about 30 mm. If the channel(s) has a semi-elliptical cross-section, at least a width 338 or a radius 340 may be less than about 30 mm. In other embodiments, the channel(s) may have at least one dimension that is less than about 25 mm, less than about 20 mm, less than about 15 mm, less than about 10 mm, less than about 9 mm, less than about 8 mm, less than about 7 mm, less than about 6 mm, less than about 5 mm, less than about 4 mm, less than about 3 mm, less than about 2 mm, or even less than about 1 mm.

In embodiments a dimension of a channel may be within particular size ranges. For example, in some embodiments, the dimension may be between about 0.1 mm to about 10 mm, between about 0.2 mm to about 9 mm, between about 0.3 mm to about 8 mm, between about 0.4 mm to about 7 mm, between about 0.5 mm to about 6 mm, between about 0.6 mm to about 5 mm, between about 0.7 mm to about 4 mm, or even between about 0.8 mm to about 3 mm. In other embodiments, the dimension may be between about 0.5 mm to about 5 mm, between about 0.6 mm to about 3 mm, the dimension may be between about 0.7 mm to about 2 mm, or even between about 0.75 mm to about 1.5 mm.

In embodiments, a flow cell may include a number of manipulation elements that are in fluid communication with each other, e.g., in series. The manipulation elements may each have a separation zone, reorienting zone, and recombining zone. In embodiments, the manipulation elements may have similar geometries, while in other embodiment, the manipulation elements may have different geometries. In embodiments, the number of manipulation elements in the flow cell may be selected in order to optimize/control factors such as: treatment time and manipulation amounts. In embodiments, in order to ensure that the fluid may be well manipulated and have sufficient treatment time in the flow cell, the flow cell may comprise greater than or equal to about 50 manipulation elements. In other embodiments, the flow cell may comprise greater than or equal to about 100 manipulation elements, greater than or equal to about 150 manipulation elements, or even greater than or equal to about 200 manipulation elements.

In other embodiments, having too many manipulation elements may result in overexposure during treatment or over manipulation of the fluid. Accordingly, in some embodiments, the flow cell may comprise less than or equal to about 5000 manipulation elements. In other embodiments, the flow cell may comprise less than or equal to about 4000 manipulation elements, less than or equal to about 3000 manipulation elements, less than or equal to about 2500 manipulation elements, less than or equal to about 2000 manipulation elements, less than or equal to about 1500 manipulation elements, less than or equal to about 1000 manipulation elements, or even less than or equal to about 500 manipulation elements. In some embodiments, two or more flow cells may be connected in series or parallel. Each flow cell may have any number of manipulation elements.

Referring to FIG. 2C, 2G, and 2H, in embodiments, flow cells may be made from two pieces of material, a first piece 204, 353, and 373 and a second piece 208, 355, and 375. The pieces may be made from materials that are transmissive to electromagnetic energy, e.g., wavelength of light such as ultraviolet and/or visible light. For example, the first pieces 204, 353, and 373 and second pieces 208, 355, and 375 may be made from polymers, glasses, ceramics, composites, or combinations thereof. In some embodiments, the first pieces 204, 353, and 373 and second pieces 208, 355, and 375 may be made from a polymeric material that is transmissive to a predetermined wavelength of light (e.g., ultraviolet, violet, indigo, blue, green, etc.). In these embodiments, the fluid may be exposed to light and be treated (e.g., pathogen reduced or cells in the fluid affected) by the light while the fluid flows through the flow cell and is manipulated by the manipulation elements. In these embodiments, one or more channel(s), separation zones, reorienting zones, and/or recombining zones may be substantially transmissive to electromagnetic energy, e.g., at least one wavelength of light. This may provide for more thorough treatment of the fluid than other conventional systems.

Examples of polymeric materials that may be used in some embodiments include, but are not limited, to acrylics, polycarbonates, vinyls (e.g., polyvinyl chloride), Ethylene-vinyl acetate (EVA) 1,2-Cyclohexane dicarboxylic acid, diisononyl ester (DINCH), and/or combinations thereof. In embodiments, both pieces 204, 353, 373, and pieces 208, 353, 373 may be made from the same, or similar, material. In other embodiments, pieces 204, 353, 373, and pieces 208, 353, 373 may be made from different materials. In one embodiment, first piece 204, 353, 373, and second piece 208, 355, and 375 may be made from a polymeric material that is transmissive to light with wavelengths that range between about 10 nm to about 800 nm. In embodiments, the pieces may be any suitable thickness. For example, in some embodiments, the pieces may have thicknesses that range from about 0.1 mm to about 2 mm.

As shown in FIG. 2, first piece 204 and second piece 208 may be attached to create flow cell 200. In some embodiments, pieces 204 and 208 may be attached around their perimeters. That is, a portion of piece 204 around its perimeter may be attached to a portion of piece 208 around its perimeter, such as for example by an adhesive, solvent welding, RF welding, ultrasonic welding, laser welding, etc. In embodiments, the first piece 204 and the second piece 208 may be injection molded. In some embodiments, it may be that only the perimeter of pieces 204 and 208 are attached, and no portions of the interior of pieces 204 and 208 are attached together. In these embodiments, a clamping mechanism, may be used to apply pressure to flow cell 200 to push piece 204 and piece 208 together particularly in the interior where the two pieces may not be attached. The pressure aids in maintaining the dimension of features of the manipulation elements.

In other embodiments, the first pieces 353 and 354 and the second pieces 355 and 375 may be sheets of material (e.g., flexible sheets) that may be shaped (e.g., by vacuum, pressure, or force) and RF welded to form flow cells 350 and 370. For example, in embodiments, two dies that create the structural features of the manipulation elements 352 and 372, may be used to form flow cells 350 and 370, including the features of the manipulation elements, for example. In some embodiments, the flow cells 350 and 370 may be flexible as a result of the first pieces 353 and 373 and the second pieces 355 and 375 being made from flexible sheet(s) of material.

Flow cells 200, 350 and 370 are shown as constructed from two pieces. However, these are merely examples of how a flow cells may be constructed according to embodiments. In other embodiments, flow cells 200, 350 and 370 may be constructed from one piece or more than two pieces. For example, in embodiments, flow cells 200, 350 and 370 may be shaped and RF welded from a sheet of material that may be folded to create two sides of the flow cells 200, 350 and 370.

Figure 4:
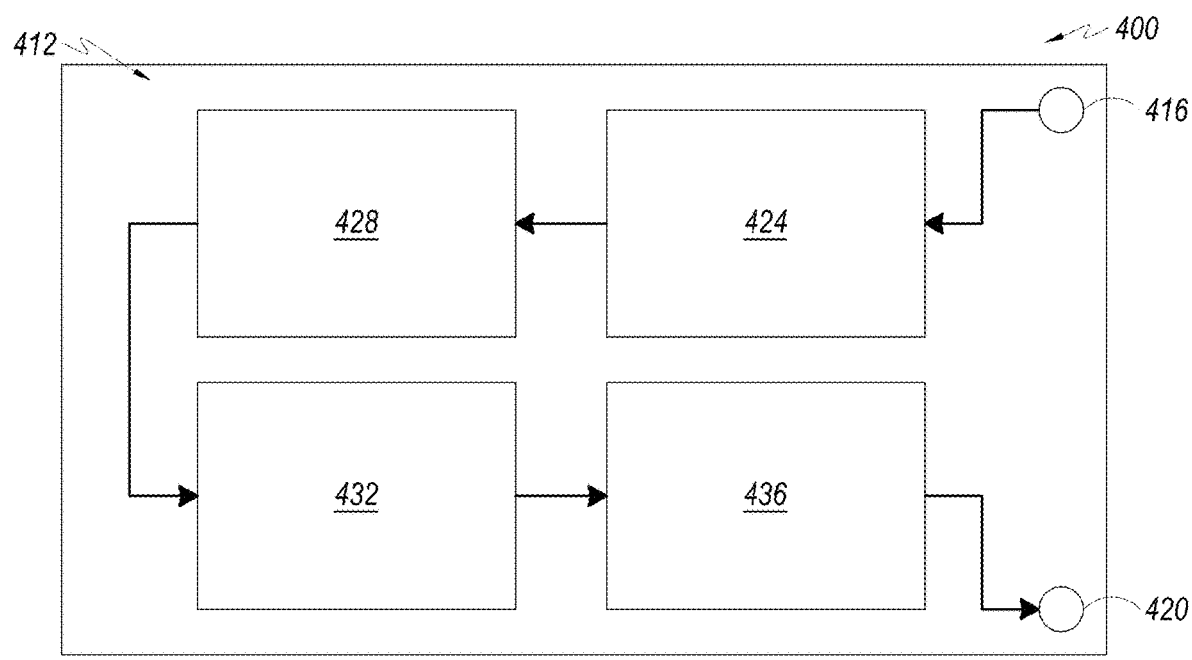
FIG. 4 illustrates a flow cell according to embodiments.

Referring now to FIG. 4, another embodiment of a flow cell 400 is illustrated. Flow cell 400 includes a number of manipulation elements 412, an inlet port 416, and an outlet port 420. Embodiments of flow cell 400 provide for manipulation elements 412 of different geometries. For purposes of illustration, the mixing elements 412 are shown in four groups 424, 428, 432, and 436. Each of the four groups may include a number of manipulation elements of a particular geometry. In some embodiments, the manipulation elements in one or more of the groups may be similar.

The geometry of some of the manipulation elements may be similar to any of elements 212, 352, 372, 700, 800, 900, 1000, 1100, 1200, 1300, 1400, or 1500 in embodiments. That is, a separation zone may comprise a splitter which separates the first flow of fluid into a second flow and a third flow. A reorienting zone may include one or more elbows that reorient second flow. The reorienting zone may further include one or more elbows that reorient third flow. The second flow and third flow may then be recombined in a recombining zone.

Other manipulation elements may have different geometries (e.g., any one of 212, 352, 372, 700, 800, 900, 1000, 1100, 1200, 1300, or 1400, 1500) one or more elbows from the first manipulation elements. The differences may be in the separation zones with a different 3-way splitters. The reorienting zone may comprise other combinations of steps, elbows, splitters, junctions, channels, or other features that reorient one or more of the second flow of fluid and the third flow of fluid either vertically and/or horizontally. The recombining zone may also have different structural features.

As one example, manipulation elements 412 in group 424 may have a first geometry that separates, reorients, and recombines fluid in one way. After flowing through manipulation elements 412 in group 424, the fluid may flow through manipulation elements 412 in group 428. In some embodiments, the manipulation elements 412 of group 428 may be similar so that the fluid is once again separated, reoriented, and recombined in the same way.

In other embodiments, the manipulation elements 412 in group 428 may have different geometries. The differences may be with respect to the separation, reorienting, and/or recombining zones of the manipulation elements 412 in group 428, e.g., different steps, elbows, splitters, junctions, channels, etc. In other embodiments, the differences may, additionally or alternatively, be with respect to channel(s) features. For example, in embodiments, channel(s) in the manipulation elements 412 of group 428 may have different dimensions. That is, a cross-section of the channel(s) in the manipulation elements of group 424 may have a first dimension that is at least a first value. A cross-section of the channel(s) in the manipulation elements of group 428 may have at least a second dimension that is at least a second value, which is different from the first value, e.g., smaller or larger. In yet another example, the cross-sectional shape of channel(s) in the manipulation elements 412 of group 428 may have a shape that is different than the cross-sectional shape of channel(s) in the elements of group 424, in addition to, or in lieu of, other differences.

After the fluid flows through manipulation elements 412 in group 428, it may flow through manipulation elements 412 of group 432. The manipulation elements 412 of group 432 may in some embodiments be similar to the manipulation elements 412 of group 424 and/or of group 428. In other embodiments, the manipulation elements of group 432 may have different geometries from one or more of the manipulation elements in group 424 or group 428. The differences may be with respect to the separation, reorienting, and/or recombining zones of the manipulation elements 412 in group 424 and/or group 428, e.g., different steps, elbows, splitters, junctions, channels etc. (e.g., elements 212, 352, 372, 700, 800, 900, 1000, 1100, 1200, 1300, 1400, or 1500). In other embodiments, the differences may, additionally or alternatively, be with respect to channel(s) features. For example, in embodiments, channel(s) in the manipulation elements 412 of group 432 may have different dimensions. That is, a cross-section of the channel(s) in the manipulation elements of group 424 may have a first dimension that is at least a first value and the manipulation elements of group 428 may have a second dimension that is at least a second value. A cross-section of the channel(s) in the manipulation elements of group 432 may have at least a third dimension that is at least a third value, which may be different from the first value and/or the second value, e.g., smaller or larger. In yet another example, the cross-sectional shape of channel(s) in the manipulation elements 412 of group 432 may have a shape that is different than the cross-sectional shape of channel(s) in the elements of group 424 and/or 428, in addition to, or in lieu of, other differences.

Similarly, after fluid flows through manipulation elements 412 in group 432, it may flow through manipulation elements 412 of group 436. The manipulation elements 412 of group 436 may in some embodiments be similar to the manipulation elements 412 of one or more of group 424, group 428, and/or group 432. In other embodiments, the manipulation elements of group 436 may have different geometries from one or more of group 424, group 428, and/or group 432. The differences may be with respect to the separation, reorienting, and/or recombining zones of the manipulation elements 412 in one or more of group 424, group 428, and/or group 432, e.g., different steps, elbows, splitters, junctions, channels etc. (e.g., elements 212, 352, 372, 700, 800, 900, 1000, 1100, 1200, 1300, 1400, or 1500). In other embodiments, the differences may, additionally or alternatively, be with respect to channel(s) features. For example, in embodiments, channel(s) in the manipulation elements 412 of group 436 may have different dimensions. That is, a cross-section of the channel(s) in the manipulation elements of group 424 may have a first dimension of a first value, group 428 may have a second dimension of a second value, and/or group 432 may have a third dimension that is at least a third value. A cross-section of the channel(s) in the manipulation elements of group 436 may have at least a fourth dimension that is at least a fourth value, which may be different from the first value, second value, and/or third value, e.g., smaller or larger. In yet another example, the cross-sectional shape of channel(s) in the manipulation elements 412 of group 436 may have a shape that is different than the cross-sectional shape of channel(s) in the elements of one or more of group 424, group 428, and/or group 432, in addition to, or in lieu of, other differences.

FIG. 4 and the description above are provided for illustrative purposes, and any combination of different manipulation elements (of different geometries, channel features, etc.) may be used with embodiments. For example, in embodiments, groups 424 and 428 may include large flow cross-section where velocities of the flow of fluid may be low and thus manipulation may be more ideal. This may be followed by groups 432 and 436 where the flow cross-section may be reduced to increase velocities to impose more inertial manipulation of the flow of fluid.

In some embodiments, groups 424, 428, 432, and 436 may represent only one manipulation element. For example, in some embodiments, a flow cell may have one manipulation element of a first geometry followed by a manipulation element of a second geometry. This may then be followed by elements with the first geometry, second geometry, or a third geometry. Any combination of different manipulation element geometries (one or more elements) in series or parallel may be used in embodiments.

Figure 5A:
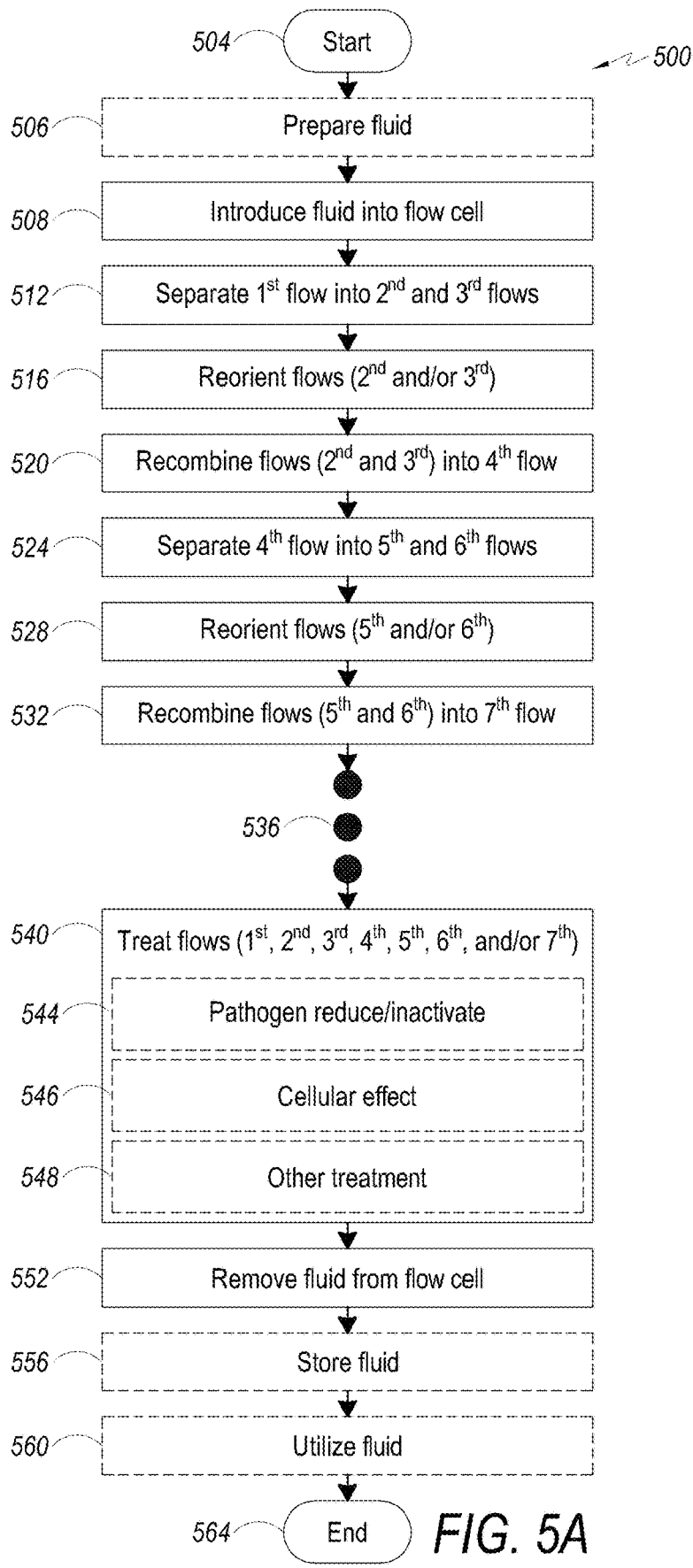
FIG. 5A illustrates a flow chart of a process of treating a fluid according to embodiments.

FIG. 5A illustrates a flow chart 500 of a process of treating a fluid according to an embodiment. In some embodiments, the fluid may be a biological fluid that may be treated to reduce pathogens in the fluid or to affect cells in the fluid. Other embodiments may provide for treating fluid by exposing to energy (e.g., illuminated, irradiated, heated, etc.), cooled, component transferred (e.g., component removed, component added), components of fluid distributed, mixing, components of fluid in close contact etc. These are merely some examples and the steps of flow chart 500 may be used in other processes to treat other fluids. Although features of flow cells (e.g., flow cells 200, 350 and 370) and/or flow systems (e.g., system 100, system 150) may be described as part of performance of the steps of the flow chart 500, embodiments are not limited thereto. Indeed, other types of flow cells, holders, clamping mechanisms, and/or systems may be used (with different structures) in the process of performing the steps of flow chart 500. In other embodiments different flow cells (with different manipulation elements), holders, clamping mechanisms, and/or systems may be used.

Flow chart 500 starts at 504 and passes to an optional step 506, where fluid may be prepared. In embodiments, steps may be performed to prepare a fluid for processing by flow 500. As one example, an additional component (e.g., a photosensitizer) may be added to a fluid at optional step 506. In embodiments, components may be removed from an initial fluid at optional step 506. For example, a separation process (e.g., an apheresis process) may be performed on blood to remove some blood components from a fluid before the fluid is processed by flow 500.

At step 508 a first flow of fluid to be treated is introduced into a flow cell at a flow rate. In embodiments, the flow cell may include a plurality of manipulation elements such as elements 212, 352, 372, 700, 800, 900, 1000, 1100, 1200, 1300, 1400, or 1500. In one embodiment, the flow cell may be similar to flow cell 200, noted above. The plurality of manipulation elements may provide features that manipulate the fluid, as described below. In some embodiments, the plurality of manipulation elements may have similar geometries. In other embodiments, the manipulation elements may include some with similar geometries and others that have different geometries.

The flow rate may be determined by a number of parameters, such as the fluid, treatment time, characteristics of the flow cell, etc. In embodiments, the first flow rate may be between about 1 ml/min to about 1000 ml/min. In some embodiments, the first flow rate may be less than about 2000 ml/min, less than about 1500 ml/min, less than about 1000 ml/min, less than about 500 ml/min, or even less than about 200 ml/min. In other embodiments, the flow rate may be between about 1 ml/min to about 100 ml/min. The flow rates may vary with the type of fluid, treatment process, volume of fluid, etc. For example, in embodiments for treating fluids that include cells (e.g., red blood cells or white blood cells), the flow rates may be slower to allow for energy to penetrate into a fluid flow since cells may be opaque to energy being used in a treatment process. Processes for treating fluids that include components (e.g., water or plasma) that are more transmissive, or transparent, to an energy source may use higher flow rates.

After step 508, flow 500 passes to step 512, where the first flow of fluid introduced into the flow cell at step 508 is separated into a second flow and a third flow. In embodiments, the separating may be performed by a separation zone of a manipulation element. In one embodiment, a manipulation element may include a separation zone that comprises a splitter, e.g., a 3-way splitter. For example, referring to FIG. 2D, manipulation elements 212A includes a separation zone 236 that may comprise a splitter which may separate the first flow of fluid 222 into second flow 228 and third flow 232.

Flow 500 then passes from step 512 to step 516, where the second flow of fluid and/or the third flow of fluid may be reoriented. The reorientation may be with respect to a direction (horizontal or vertical) that the second flow or third flow has after separation. The second and/or third flows may be reoriented horizontally, vertically, at some angle (0 degrees to 180 degrees) with respect to horizontal or vertical, on a same plane, on a different plane, or a combination thereof. In embodiments, the reorienting may be performed in a reorienting zone of a manipulation element. The reorienting zone may include combinations of steps, elbows, splitters, junctions, channels, or other features that reorient one or more of the second flow of fluid and the third flow of fluid. As one example, referring to FIG. 2D, reorienting zone 240 may include elbow(s) that reorient second flow 228 vertically back to an initial plane and an elbow that reorients second flow 228 90 degrees. The reorienting zone 240 may further include an elbow that reorients third flow 232 90 degrees and an elbow that reorients third flow 232 up to a different plane.

Figure 5B:
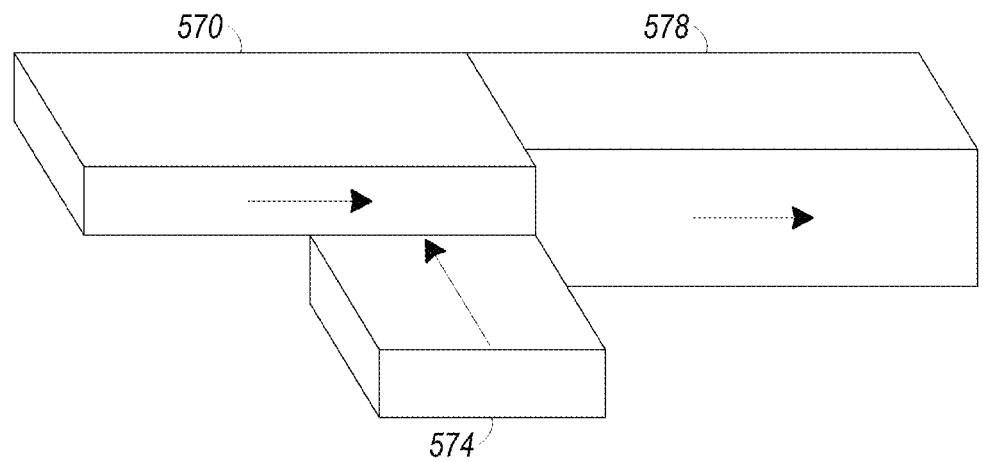
FIG. 5B illustrates two flows recombined by being stacked together according to embodiments.
Figure 5C:
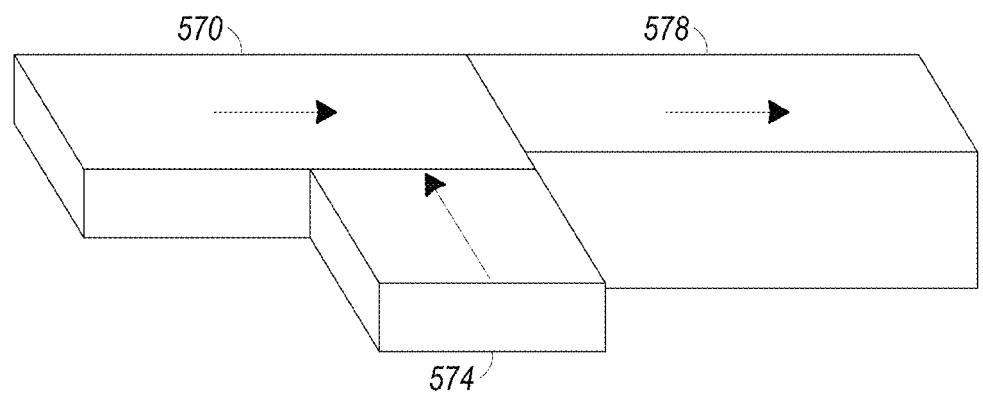
FIG. 5C illustrates two flows recombined by being folded together according to embodiments.

After step 516, the process passes to step 520 where the second flow of fluid and the third flow of fluid may be recombined to form a fourth flow. The second and third flows may be recombined by being stacked with each other, folded together on a same plane, or a combination. As one example, FIG. 5B illustrates a flow 570 being stacked with flow 574 to form flow 578. FIG. 5C illustrates a different example showing flow 570 being folded with flow 574 to form flow 578. In embodiments, the second and third flows may be substantially perpendicular to each other when recombined (e.g., recombining zone 244) as shown in FIGS. 5B and 5C. In other embodiments, the second and third flows may be substantially parallel to each other when recombined. In yet other embodiments, the second and third flows may be recombined at some angle. The recombining step 520 may be performed by a recombing zone of a manipulation element. The recombining zone may include combinations of steps, elbows, splitters, junctions, channels, or other features that recombine the second flow of fluid with the third flow of fluid. As one example, referring to FIG. 2D, recombining zone 244 includes a junction that provides for third flow 232 to be stacked with second flow 228. In the embodiment shown in FIG. 2D, the third flow and the second flow may be substantially perpendicular when stacked at recombining zone 244.

After step 520, flow 500 passes to step 524, where the fourth flow of fluid formed at step 520 is separated into a fifth flow and a sixth flow. In embodiments, the separating may be performed by a separation zone of a manipulation element. In one embodiment, a manipulation element may include a separation zone that comprises a splitter, e.g., a 3-way splitter. For example, referring to FIG. 2D, manipulation element 212B includes a separation zone 252 that may comprise a splitter which separates the fourth flow of fluid into fifth flow 256 and sixth flow 260.

Flow 500 then passes from step 524 to step 528, where the fifth flow of fluid and/or the sixth flow of fluid may be reoriented. The reorientation may be with respect to a direction (horizontal or vertical) that the fifth flow or sixth flow has after separation. The fifth and/or sixth flows may be reoriented horizontally, vertically, at some angle (0 degrees to 180 degrees) with respect to horizontal or vertical, on a same plane, on a different plane, or a combination thereof. In embodiments, the reorienting may be performed in a reorienting zone of a manipulation element. The reorienting zone may include combinations of steps, elbows, splitters, junctions, channels, or other features that reorient one or more of the fifth flow of fluid and the sixth flow of fluid. As one example, referring to FIG. 2D, reorienting zone 264 includes elbows that reorient fifth flow 256: vertically back to an initial plane and 90 degrees. The reorienting zone 264 further includes elbows that reorient sixth flow 260 to a different plane and 90 degrees. The reorienting zone 264 further includes an elbow that reorients sixth flow 260 back to an initial plane.

The process 500 passes to step 532 where the fifth flow of fluid and the sixth flow of fluid may be recombined to form a seventh flow of fluid. The fifth and sixth flows may be recombined by being folded together on a same plane, stacked, or a combination. In embodiments, the fifth and sixth flows may be substantially perpendicular to each other when recombined (e.g., recombining zone 268). In other embodiments, the second and third flows may be substantially parallel to each other when recombined. In yet other embodiments, the second and third flows may be recombined at some angle (0 degrees to 180 degrees) with respect to each other. The recombining step 532 may be performed by a recombining zone of a manipulation element. The recombining zone may include combinations of steps, elbows, junctions, splitters, channels, or other features that recombine the fifth flow of fluid with the sixth flow of fluid. As one example, referring to FIG. 2D, recombining zone 268 includes a junction that provides for fifth flow 256 to be folded into sixth flow 260. In the embodiment shown in FIG. 2D, the fifth flow and the sixth flow are substantially perpendicular when folded into each other by recombining zone 268.

As part of process 500, the steps of separate, reorient, and recombine flows may be performed an additional number of times as illustrated by ellipsis 536. The steps of separate, reorient, and recombine may be performed sequentially a predetermined number of times. For example, in some embodiments, the steps may be performed greater than or equal to about 50 times. In other embodiments, the steps may be performed greater than or equal to about 100 times, greater than or equal to about 150 times, or even greater than or equal to over 200 times. In other embodiments, the steps may be performed less than or equal to about 5000 times, less than or equal to about 4000 times, or even less than or equal to about 3000 times. In other embodiments, the steps may be performed less than or equal to about 2500 times, less than or equal to about 2000 times, less than or equal to about 1500 times, less than or equal to about 1000 times, or even less than or equal to about 900 times. In embodiments, the steps may be performed between about 50 times and about 4000 times, such as between about 100 times and about 3000 times.

FIGS. 2A-2F and 7A-15B illustrate geometries of manipulation elements that may be used to perform one or more of the steps: separate, reorient, and recombine flows of flow 500. In embodiments, the separate, reorient, and recombine flows steps are performed to provide ordered (e.g., laminar) manipulation. Separating, reorienting, and recombining fluid may be performed to thoroughly manipulate the fluid and expose substantially all of the fluid to a surface. In other words, the steps are performed to ensure that substantially all of the fluid, as it is processed by flow 500, travels to the surface for some period of time to ensure the fluid is treated (e.g., exposed to energy (illuminated, irradiated, heated), cooled, components removed or added, etc.). In some embodiments, the manipulation may result in thorough mixing of the fluid. In embodiments, the steps of 500 may all involve laminar flow of fluid and not involve turbulent flow of fluid.

From ellipsis 536, process 500 passes to step 540, where flows may be treated. Embodiments may provide for step 540 to include a number of optional substeps. The substeps may depend on the treatment that may be performed on the fluid. In embodiments, the treatment may involve reducing/ inactivating pathogens in a fluid 544, affecting cells in a fluid 546, and/or other treatments 548. The substeps may involve performing steps that effect the desired treatment. For example, the substeps may, in embodiments, involve exposing the fluid to energy (such as illuminated, irradiated, heated, etc.), cooling the fluid, and/or removing or adding components to a fluid etc. In embodiments, step 540 may be performed on one or more of the flows (e.g., $1^{st}$-$7^{th}$) as one or more of the steps 508-536 are performed. In other embodiments, step 540 may be performed during the performance of all of the steps 508-536. For example, in one embodiment, steps 508-536 may be performed by a flow cell with a number of manipulation elements. As the fluid flows through the flow cell, it may be treated. In these embodiments, the treatment step 540 may be performed during each step of separating flows, reorienting flows, and recombining flows. As may be appreciated, these embodiments may provide treatment of the fluid as it is being manipulated. As one non-limiting example of a possible treatment for treating fluids, process 500 may include an optional step 544 where pathogens in the fluid may be reduced/inactivated. In embodiments, the reduction in pathogens may be affected by the illumination of the fluid. In some embodiments, the light alone may create a pathogen reducing effect. In other embodiments, an additional material, may work in combination with the light energy to affect the pathogen reduction. In embodiments, the fluid treated with process 500 may contain an additional material, e.g., a photosensitizer that aids in pathogen reduction. The additional material may have been added at optional step 506 or during some other step. Without being bound by theory, it is believed that photosensitizers include molecules that may be activated by light energy (e.g., ultraviolet light). The photosensitizer (or reaction products resulting from the activation) may disrupt bonds in DNA. In pathogens, for example, but not limited to, various viruses and bacteria, the disruption may lead to the death of the pathogen, an inability to reproduce, or otherwise inactivation. Some non-limiting examples of photosensitizers that may be used in some embodiments include: porphyrins, flavins (e.g., riboflavin), psoralens (e.g., 8-methoxypsoralen), acridine, toluidines, phenothiazine derivatives, dyes (e.g., natural red, methylene blue, etc.), and combinations thereof.

As another non-limiting example of a possible treatment, optional step 546 may involve steps for affecting cells in a fluid, e.g., photopheresis. In some embodiments, an additional material, may work in combination with light energy to affect cells in the fluid. Without being bound by theory, it is believed that light energy may activate a photosensitizer and may cause cross linkage of DNA which may reduce the activity of cells (e.g., white blood cells), which may, for example, reduce an undesired immune response. Some non-limiting examples of photosensitizers that may be used in some embodiments include: porphyrins, flavins (e.g., riboflavin), psoralens (e.g., 8-methoxypsoralen), acridine, toluidines, phenothiazine derivatives, dyes (e.g., natural red, methylene blue, etc.), and combinations thereof.

Step 540 may involve the use of light in the ultraviolet spectrum such as light with a wavelength of between about 100 nm and about 400 nm. In other embodiments, the light used in step 540 may be in the visible light spectrum such as with wavelengths of between about 300 nm and about 800 nm. In yet other embodiments, the light used in step 540 may be a combination of ultraviolet and visible light, for example with wavelengths of between about 100 nm and about 500 nm. In other embodiments, light used at step 540 may include UVA (wavelengths from about 315 nm to about 400 nm), UVB (wavelengths from about 280 nm to about 315 nm) and/or UVC (wavelengths from about 100 nm to about 280 nm). Other embodiments provide for use of light with wavelengths from about 10 nm to about 450 nm. Other non-limiting examples of possible wavelengths of light that may be used at step 540 include, visible light such as violet light (wavelengths from about 400 nm to about 420 nm), indigo light (wavelengths from about 420 nm to about 440 nm), blue light (wavelengths from about 440 nm to about 490 nm), green light (wavelengths from about 490 nm to about 570 nm), yellow light (wavelengths from about 565 nm to about 590 nm), orange light (wavelengths from about 590 nm to about 625 nm), red light (wavelengths from about 625 nm to about 740 nm). In embodiments, light in any of the ranges noted above or in any combination of the ranges listed above may be used in step 540.

In yet other embodiments, other substeps may be performed when utilizing other treatments 548 to treat the fluid. Some non-limiting examples of other treatments include: molecule transfer, heating, cooling, exposing to energy, physical addition of components, physical removal of components, distribution of components in a fluid, intimate contact of components in a fluid, etc.

Flow 500 then moves to step 552 where the fluid, which is now treated, is removed from the flow cell. Step 552 may be followed by optional steps. For example, at step 556 the treated fluid may be stored. The treated fluid may be stored in a container, e.g., bottle or bag. The container may be refrigerated for longer storage. At optional step 560, the fluid may be used. In embodiments, step 560 may involve administering the fluid to a patient for therapeutic purposes. For example, the fluid may be infused, injected, ingested, or applied to a patient. For example, if the fluid is whole blood or a component of whole blood, the fluid may be infused into a patient. In other embodiments, the fluid may be used for testing or other experimental uses. Flow 500 then ends at 564.

Although flow chart 500 has been described with steps listed in a particular order, the embodiments are not limited thereto. In other embodiments, steps may be performed in different order, in parallel, or any different number of times, e.g., before and after another step. Also, flow chart 500 may include some optional steps or sub-steps. However, those steps above that are not indicated as optional should not be considered as essential to the invention but may be performed in some embodiments of the present invention and not in others.

Figure 6:
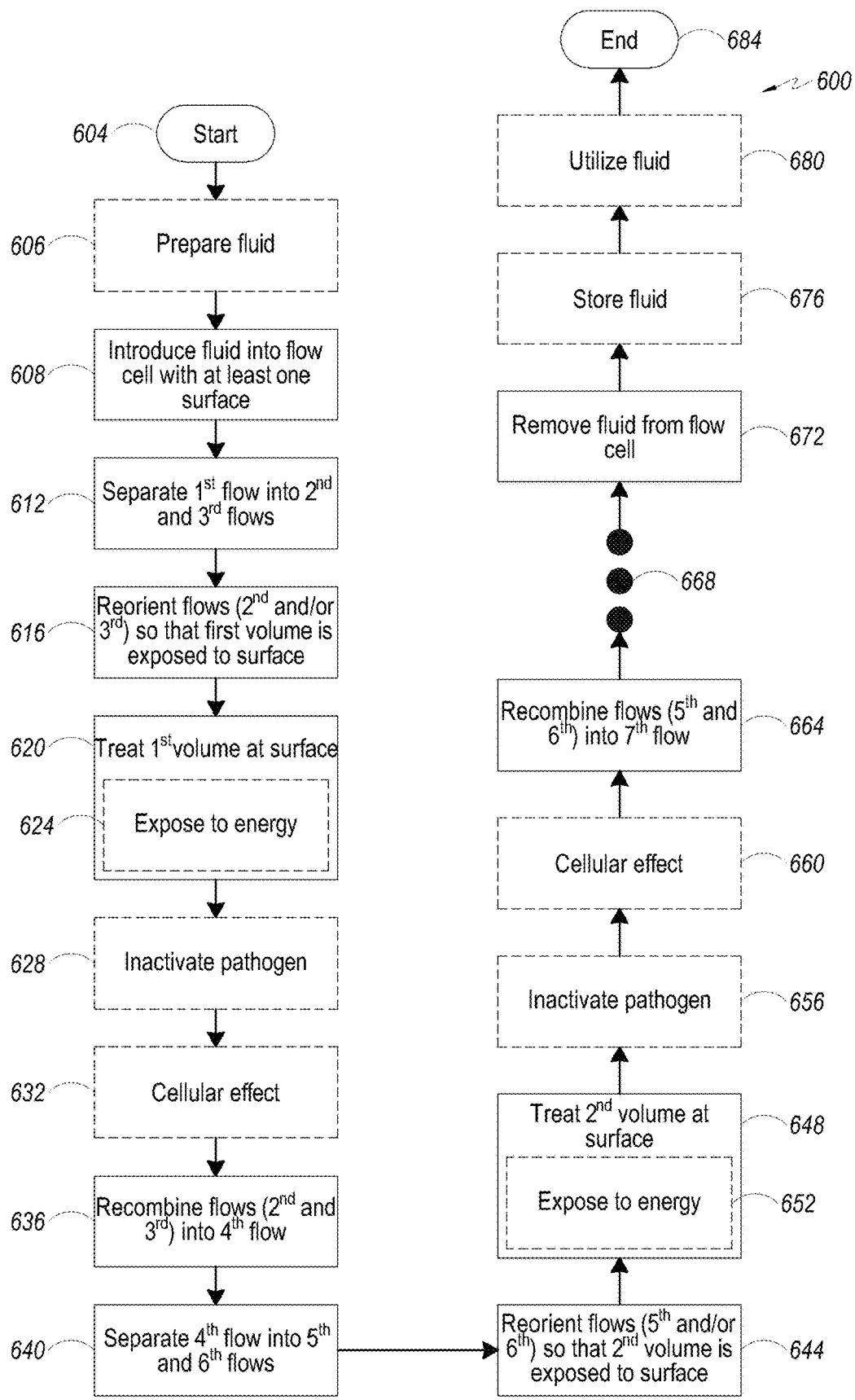
FIG. 6 illustrates a flow chart of a process of treating a fluid according to embodiments.

FIG. 6 illustrates a flow chart 600 of a process of treating a fluid according to another embodiment. In some embodiments, the fluid may be a biological fluid that may be treated to reduce pathogens in the fluid or to affect cells in the fluid. Other embodiments may provide for treating fluid by exposing to energy (e.g., illuminated, irradiated, heated, etc.), cooled, component transferred (e.g., component removed, component added), component of fluid distributed, components of fluid in close contact, etc. These are merely some examples and the steps of flow chart 600 may be used in other processes to treat other fluids. Although features of flow cells (e.g., flow cells 200, 350 and 370) and/or flow systems (e.g., system 100, system 150) may be described as part of performance of the steps of the flow chart 600, embodiments are not limited thereto. Indeed, other types of flow cells (with different manipulation elements), holders, clamping mechanisms, and/or systems may be used (with different structures) in the process of performing the steps of flow chart 600.

Flow chart 600 starts at 604 and passes to an optional step 606, where fluid may be prepared. In embodiments, steps may be performed to prepare a fluid for processing by flow 600. As one example, a material (e.g., a photosensitizer) may be mixed with a fluid at optional step 606. In embodiments, components may be removed from an initial fluid at optional step 606. For example, a separation process (e.g., an apheresis process) may be performed on blood to remove some blood components from a fluid before the fluid is processed by flow 600.

Flow passes to step 608 where a first flow of fluid to be treated is introduced into a flow cell at a flow rate. In embodiments, the flow cell may include a plurality of manipulation elements such as elements 212, 352, 372, and/or 412. In one embodiment, the flow cell may be similar to flow cell 200, noted above. The plurality of manipulation elements may provide features that manipulate the fluid, as described below. In some embodiments, the plurality of manipulation elements may have similar geometries. In other embodiments, the manipulation elements may include some with similar geometries and others that have different geometries.

The flow rate may be determined by a number of parameters, such as the fluid, treatment time, characteristics of the flow cell, etc. In embodiments, the first flow rate may be between about 1 ml/min to about 1000 ml/min. In some embodiments, the first flow rate may be less than about 2000 ml/min, less than about 1500 ml/min, less than about 1000 ml/min, less than about 500 ml/min, or even less than about 200 ml/min. In other embodiments, the flow rate may be between about 1 ml/min to about 100 ml/min. For example, in embodiments for treating fluids that include cells (e.g., red blood cells or white blood cells), the flow rates may be slower to allow for energy to penetrate into a fluid flow since cells may be opaque to energy being used in a treatment process. Processes for treating fluids that include components (e.g., water or plasma) that are more transmissive, or transparent, to an energy source may use higher flow rates.

After step 608, flow 600 passes to step 612, where the first flow of fluid introduced into the flow cell at step 608 is separated into a second flow and a third flow. In embodiments, the separating may be performed by a separation zone of a manipulation element. In one embodiment, a manipulation element may include a separation zone that comprises a splitter, e.g., a 3-way splitter. For example, referring to FIG. 2D, manipulation elements 212A includes a separation zone 236 that may comprise a splitter which may separate the first flow of fluid into second flow 228 and third flow 232.

Flow 600 then passes from step 612 to step 616, where the second flow of fluid and/or the third flow of fluid may be reoriented. In embodiment, the reorientation may be performed so that a first volume of fluid is exposed to one or more surfaces of a flow cell. Referring to FIG. 2E, for example, the second and/or third flow may be reoriented, so a volume of fluid is exposed to a surface, e.g., surface 204A or surface 208A.

Figure 8C:
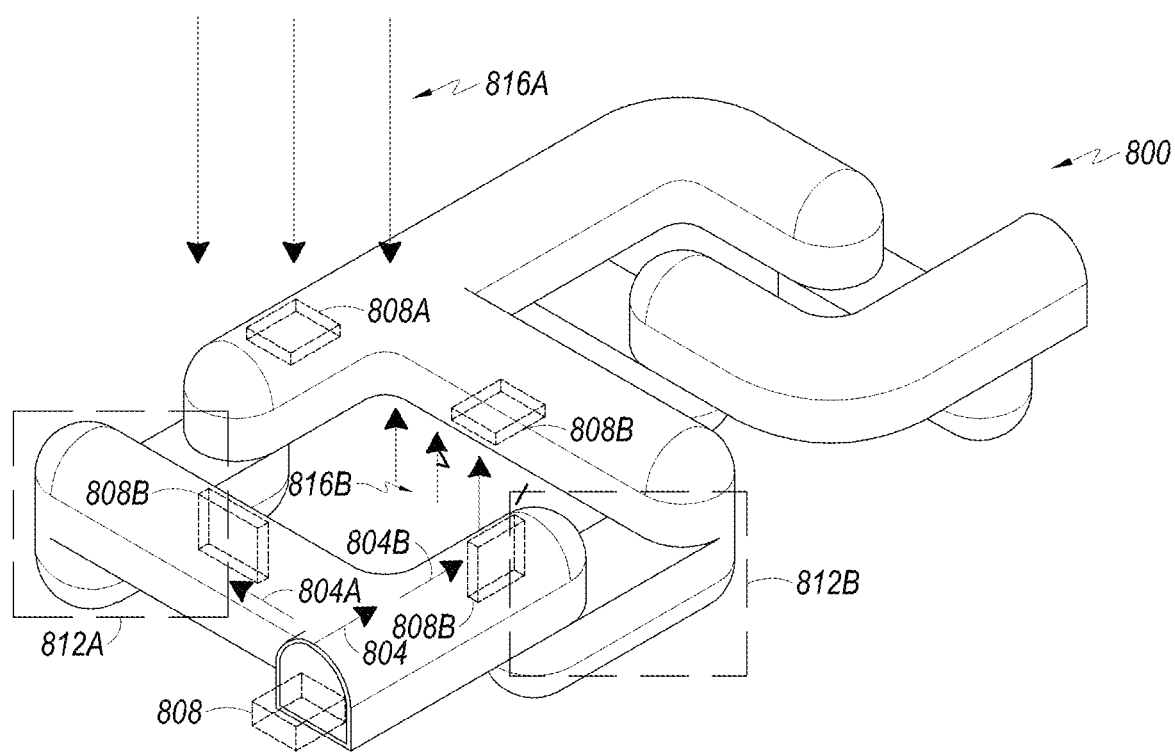
FIG. 8C illustrates a zoomed in view of a portion of FIG. 8A.

FIG. 8C illustrates how flows may be reoriented at step 616 to expose a first volume to a surface. FIG. 8C illustrated a zoomed in portion of manipulation elements 800. As shown in FIG. 8C, a first flow 804 may be separated into a second flow 804A and a third flow 804B at step 612. Flow 804 may include a volume 808 that is generally in the middle of the flow and is not exposed to a surface of a flow cell, e.g., surface 204A or surface 208B of flow cell 200. As illustrated in FIG. 8A, volume 808 may be separated into volume 808A and 808B. FIG. 8A illustrates volumes 808, 808A and 808B at various times as the volumes flow through manipulation element 800.

Flows 804A and 804B may be reoriented as part of step 616 so that volume 808A and 808B are exposed to a surface of the flow cell. As illustrated in FIG. 8A as flow 804A is reoriented by reorienting zone 812A, volume 808A becomes exposed to a surface. Similarly, flow 804B may be reoriented by reorienting zone 812B to become exposed to a surface. As illustrated in FIG. 8A, volume 808A has been reoriented so that it is exposed to a first surface, e.g., a top surface. Similarly, volume 808B has been reoriented so it is now exposed to a second surface, e.g., a bottom surface. In some embodiments, the volume (e.g., 808, 808A, and/or 808B) may not have previously been exposed to a surface. In embodiments, the volume (e.g., 808, 808A, and/or 808B) may include particles such as cells, viruses, bacteria, or other types of particles.

Process 600 passes to step 620, where the first volume may be treated at a surface. Embodiments may provide for step 600 to include a number of optional substeps. The substeps may depend on the treatment that may be performed on the fluid. In embodiments, step 620 may involve exposing the volume of fluid to energy at substep 624. As illustrated in FIG. 8A, volume 808A may be exposed to energy (illustrated by arrows 816A) directed to a first surface. Volume 808B may be exposed to energy (illustrated by arrows 816B) directed at a second surface. Substep 624 may involve illuminating, irradiating, heating, etc., the volume at a surface.

Optional step 624 may involve the use of light in the ultraviolet spectrum such as light with a wavelength of between about 100 nm and about 400 nm. In other embodiments, the light used in optional step 624 may be in the visible light spectrum such as with wavelengths of between about 300 nm and about 800 nm. In yet other embodiments, the light used in optional step 624 may be a combination of ultraviolet and visible light, for example with wavelengths of between about 100 nm and about 500 nm. In other embodiments, light used at optional step 624 may include UVA (wavelengths from about 315 nm to about 400 nm), UVB (wavelengths from about 280 nm to about 315 nm) and/or UVC (wavelengths from about 100 nm to about 280 nm). Other embodiments provide for use of light with wavelengths from about 10 nm to about 450 nm. Other non-limiting examples of possible wavelengths of light that may be used at step 624 include, visible light such as violet light (wavelengths from about 400 nm to about 420 nm), indigo light (wavelengths from about 420 nm to about 440 nm), blue light (wavelengths from about 440 nm to about 490 nm), green light (wavelengths from about 490 nm to about 570 nm), yellow light (wavelengths from about 565 nm to about 590 nm), orange light (wavelengths from about 590 nm to about 625 nm), red light (wavelengths from about 625 nm to about 740 nm). In embodiments, light in any of the ranges noted above or in any combination of the ranges listed above may be used in step 624.

In embodiments, a surface of a flow cell (and consequently fluid exposed to the surface) at step 624 may be exposed to energy at an irradiance of between about 0.5 mW/cm2 and about 100 mW/cm2. As may be appreciated, the irradiance used during a fluid treatment process may depend on other parameters such as flow rate, volume, time of exposure, etc. In some embodiments, the surface of a flow cell may be exposed to light, at step 640, at an irradiance of between about 1.0 mW/cm2 to about 500 mW/cm2, between about 2 mW/cm2 to about 400 mW/cm2, between about 3 mW/cm2 to about 300 mW/cm2, between about 4 mW/cm2 to about 200 mW/cm2, or even between about 5 mW/cm2 to about 100 mW/cm2. In other embodiments, the surface of a flow cell may be exposed to light at an irradiance of between about 1.0 mW/cm2 to about 50 mW/cm2, between about 1.5 mW/cm2 to about 25 mW/cm2, between about 2 mW/cm2 to about 20 mW/cm2, between about 2.5 mW/cm2 to about 15 mW/cm2, or even between about 3 mW/cm2 to about 10 mW/cm2. In other embodiments, the surface of a flow cell may be exposed to light at an irradiance that is less than 500 mW/cm2, less than 400 mW/cm2, less than 300 mW/cm2, less than 200 mW/cm2, or even less than 100 mW/cm2.

Process 600 may pass to optional steps that may be performed as a consequence of the treatment step 620. As one example, the fluid may include particles of pathogens (e.g., viruses, bacteria, etc.) that may be inactivated at optional step 628. In embodiments, the reduction in pathogens may be affected by the illumination of the fluid with electromagnetic energy at step 620. In some embodiments, the energy alone may create a pathogen reducing effect. In other embodiments, an additional material, may work in combination with the energy to affect the pathogen reduction. In embodiments, the fluid treated with process 600 may contain an additional material, e.g., a photosensitizer that aids in pathogen reduction. The photosensitizer may have been added at step 606 or some other step. Without being bound by theory, it is believed that photosensitizers include molecules that may be activated by electromagnetic energy (e.g., ultraviolet light). The photosensitizer (or reaction products resulting from the activation) may disrupt bonds in DNA. In pathogens, for example, but not limited to, viruses and bacteria, the disruption may lead to the death of the pathogen, an inability to reproduce, or otherwise inactivation. Some non-limiting examples of photosensitizers that may be used in some embodiments include: porphyrins, flavins (e.g., riboflavin), psoralens (e.g., 8-methoxypsoralen), acridine, toluidines, phenothiazine derivatives, dyes (e.g., natural red, methylene blue, etc.), and combinations thereof As another non-limiting example, optional step 632 may affect cells in the fluid, e.g., photopheresis. In some embodiments, an additional material, may work in combination with energy to affect cells in the fluid. The additional material may have been added at step 606 or some other step. Without being bound by theory, it is believed that electromagnetic energy (e.g., ultraviolet light) may activate a photosensitizer and may cause cross linkage of DNA which may reduce the activity of cells (e.g., white blood cells), which may, for example, reduce an undesired immune response. Some non-limiting examples of photosensitizers that may be used in some embodiments include: porphyrins, flavins (e.g., riboflavin), psoralens (e.g., 8-methoxypsoralen), acridine, toluidines, phenothiazine derivatives, dyes (e.g., natural red, methylene blue, etc.), and combinations thereof.

After optional step 632, the process passes to step 636 where the second flow of fluid and the third flow of fluid may be recombined to form a fourth flow. The second and third flows may be recombined by being stacked with each other, folded together on a same plane, or a combination. In embodiments, the second and third flows may be substantially perpendicular to each other when recombined. In other embodiments, the second and third flows may be substantially parallel to each other when recombined. In yet other embodiments, the second and third flows may be recombined at some angle with respect to each other. The recombining step 636 may be performed by a recombing zone of a manipulation element. The recombining zone may include combinations of steps, elbows, splitters, junctions, channels, or other features that recombine the second flow of fluid with the third flow of fluid. As one example, referring to FIG. 2D, recombining zone 244 includes a junction that provides for third flow 232 to be stacked with second flow 228. In the embodiment shown in FIG. 2D, the third flow and the second flow may be substantially perpendicular when stacked at recombining zone 244.

After step 636, flow 600 passes to step 640, where the fourth flow of fluid formed at step 636 is separated into a fifth flow and a sixth flow. In embodiments, the separating may be performed by a separation zone of a manipulation element. In one embodiment, a manipulation element may include a separation zone that comprises a splitter, e.g., a 3-way splitter. For example, referring to FIG. 2D, manipulation element 212B includes a separation zone 252 that may comprise a splitter which separates the fourth flow of fluid into fifth flow 256 and sixth flow 260.

Flow 600 then passes from step 640 to step 644, where the fifth flow and/or sixth flow of fluid may be reoriented. In embodiments, the reorientation may be performed so that a second volume of fluid is exposed to one or more surfaces of a flow cell. Referring to FIG. 2E, for example, the fifth and/or sixth flow may be reoriented, so the second volume of fluid is exposed to surface 204A or surface 208A.

As described above with respect to step 616, the fifth flow and/or the sixth flow may be reoriented as part of step 644 so that a second volume is exposed to a surface of the flow cell. In embodiments, the second volume may not have previously been exposed to a surface. In embodiments, the second volume may also include particles such as cells, viruses, bacteria or other types of particles.

Process 600 passes to step 648, where the second volume may be treated at a surface. Embodiments may provide for step 600 to include a number of optional substeps. The substeps may depend on the treatment that may be performed on the fluid. In embodiments, step 648 may involve exposing the second volume of fluid to energy at substep 652. Substep 652 may involve illuminating, irradiating, heating, etc., the second volume at a surface.

Process 600 may pass to optional steps that may be performed as a consequence of the treatment step 648. As one example, the fluid may include particles of pathogens (e.g., viruses, bacteria, etc.) that may be inactivated at optional step 656. In embodiments, the reduction in pathogens may be affected by the illumination of the fluid with electromagnetic energy at step 652. In some embodiments, the energy alone may create a pathogen reducing effect. In other embodiments, an additional material, may work in combination with the energy to affect the pathogen reduction. In embodiments, the fluid treated with process 600 may contain an additional material, e.g., a photosensitizer that aids in pathogen reduction. Without being bound by theory, it is believed that photosensitizers include molecules that may be activated by electromagnetic energy (e.g., ultraviolet light). The photosensitizer (or reaction products resulting from the activation) may disrupt bonds in DNA. In pathogens, for example, but not limited to, viruses and bacteria, the disruption may lead to the death of the pathogen, an inability to reproduce, or otherwise inactivation. Some non-limiting examples of photosensitizers that may be used in some embodiments include: porphyrins, flavins (e.g., riboflavin), psoralens (e.g., 8-methoxypsoralen), acridine, toluidines, phenothiazine derivatives, dyes (e.g., natural red, methylene blue, etc.), and combinations thereof.

As another non-limiting example, optional step 660 may affect cells in the fluid, e.g., photopheresis. In some embodiments, an additional material, may work in combination with energy to affect cells in the fluid. Without being bound by theory, it is believed that electromagnetic energy (e.g., ultraviolet light) may activate a photosensitizer and may cause cross linkage of DNA which may reduce the activity of cells (e.g., white blood cells), which may, for example, reduce an undesired immune response. Some non-limiting examples of photosensitizers that may be used in some embodiments include: porphyrins, flavins (e.g., riboflavin), psoralens (e.g., 8-methoxypsoralen), acridine, toluidines, phenothiazine derivatives, dyes (e.g., natural red, methylene blue, etc.), and combinations thereof.

After optional step 660, the process passes to step 664 where the fifth flow of fluid and the sixth flow of fluid may be recombined to form a seventh flow. The fifth and seventh flows may be recombined by being stacked with each other, folded together on a same plane, or a combination. In embodiments, the fifth and sixth flows may be substantially perpendicular to each other when recombined. In other embodiments, the fifth and sixth flows may be substantially parallel to each other when recombined. In yet other embodiments, the fifth and sixth flows may be recombined at some angle. The recombining step 664 may be performed by a recombing zone of a manipulation element. The recombining zone may include combinations of steps, elbows, splitters, junctions, channels, or other features that recombine the fifth flow of fluid with the sixth flow of fluid. As one example, referring to FIG. 2D, recombining zone 244 includes a junction that provides for a flow to be stacked with another flow. The fifth flow and the sixth flow may be substantially perpendicular when stacked.

As part of process 600, the steps of separate, reorient, treat, and recombine flows may be performed an additional number of times as illustrated by ellipsis 668. The steps of separate, reorient, and recombine may be performed sequentially a predetermined number of times. For example, in some embodiments, the steps may be performed greater than or equal to about 50 times. In other embodiments, the steps may be performed greater than or equal to about 100 times, greater than or equal to about 150 times, or even greater than or equal to over 200 times. In other embodiments, the steps may be performed less than or equal to about 5000 times, less than or equal to about 4000 times, or even less than or equal to about 3000 times. In other embodiments, the steps may be performed less than or equal to about 2500 times, less than or equal to about 2000 times, less than or equal to about 1500 times, less than or equal to about 1000 times, or even less than or equal to about 900 times. In embodiments, the steps may be performed between about 50 times and about 4000 times, such as about 100 times to about 3000 times.

FIGS. 2A-2F and 7A-15B illustrate geometries of manipulation elements that may be used to perform one or more of the steps: separate, reorient, and recombine flows. In embodiments, the separate, reorient, and recombine flows steps are performed to provide ordered (e.g., laminar) manipulation. Separating, reorienting, and recombining fluid may be performed to thoroughly manipulate the fluid and expose substantially all of the fluid to a surface. In other words, the steps are performed to ensure that substantially all of the fluid, as it is processed by flow 600, is exposed to the surface for some period of time to ensure the fluid is treated (e.g., exposed to energy (illuminated, irradiated, heated), cooled, components removed or added, components of the fluid distributed, components of fluid placed in intimate contact, etc.). In some embodiments, the manipulation may result in thorough mixing of the fluid. In other embodiments, fluid may maintain laminar flow during all of the steps of flow 600 and not involve turbulent flow.

From ellipsis 668, flow 600 passes to step 672 where the fluid, which is treated, is removed from the flow cell. Step 672 may be followed by optional steps. For example, at step 676 treated fluid may be stored. The treated fluid may be stored in a container, e.g., bottle or bag. The container may be refrigerated for longer storage. At optional step 680, the fluid may be used. Step 680 may involve administering the fluid to a patient for therapeutic purposes. For example, the fluid may be infused, injected, ingested, or applied to a patient. If the fluid is whole blood or a component of whole blood, the fluid may be infused into a patient. In other embodiments, the fluid may be used for testing or other experimental use. Flow 600 then ends at 684.

Although flow chart 600 has been described with steps listed in a particular order, the embodiments are not limited thereto. In other embodiments, steps may be performed in different order, in parallel, or any different number of times, e.g., before and after another step. Also, flow chart 600 may include some optional steps or sub-steps. However, those steps above that are not indicated as optional should not be considered as essential to the invention but may be performed in some embodiments of the present invention and not in others.

Figure 16:
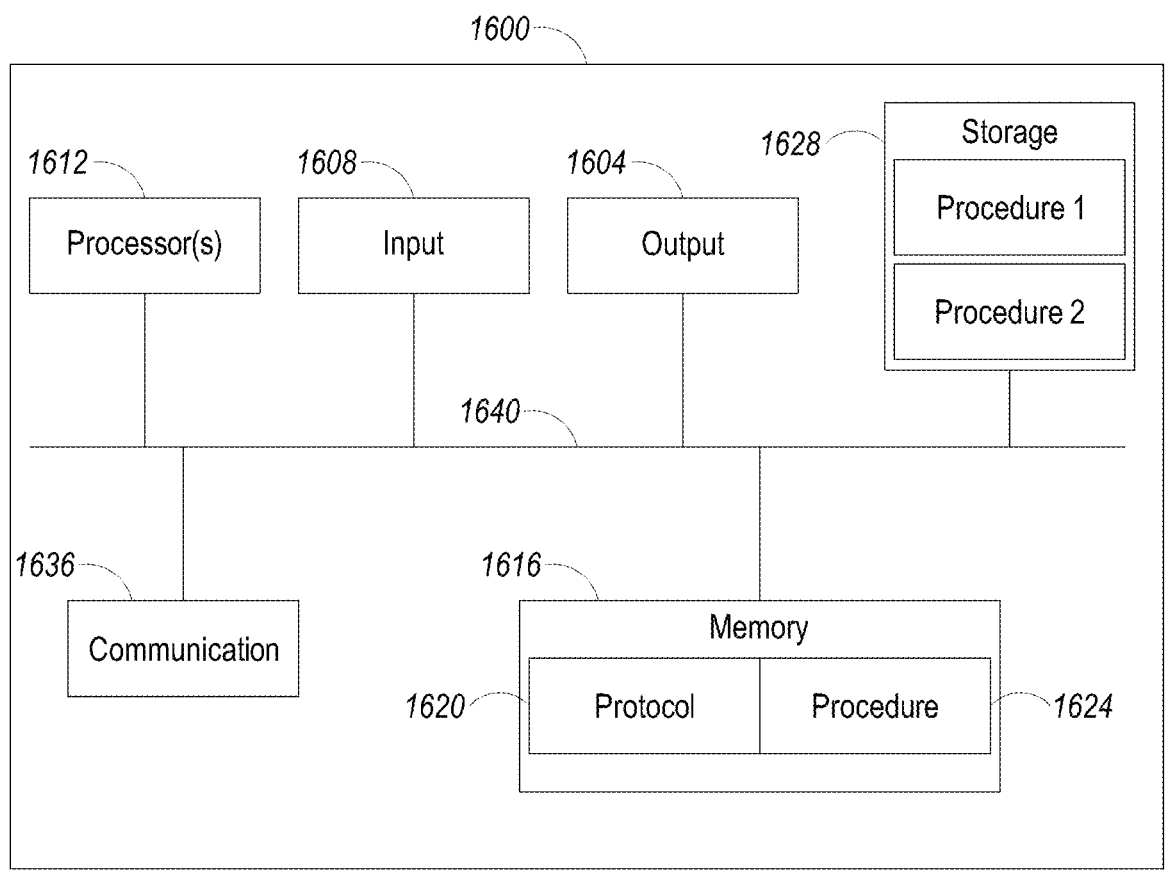
FIG. 16 illustrates a block diagram of a basic computer that may be used to implement embodiments.

FIG. 16 illustrates example components of a basic computer system 1600 upon which embodiments of the present invention may be implemented. Computer system 1600 may perform some steps in the methods for introducing fluid into a flow cell or illuminating fluid in a flow cell. System 1600 may be a controller for controlling features, e.g., flow control devices, pumps, valves, motors, lighting systems, sensors, clamping mechanisms etc., of systems such as systems 100 and/or 150 described above.

Computer system 1600 includes output device(s) 1604, and/or input device(s) 1608. Output device(s) 1604 may include one or more displays, including CRT, LCD, LED, and/or plasma displays. Output device(s) 1604 may also include a printer, speaker, etc. Input device(s) 1608 may include a keyboard, touch input devices, a mouse, voice input device, etc.

Basic computer system 1600 may also include a processing unit 1612 and/or a memory 1616, according to embodiments of the present invention. The processing unit 1612 may be a general-purpose processor operable to execute instructions stored in memory 1616. Processing unit 1612 may include a single processor or multiple processors, according to embodiments. Further, in embodiments, each processor may be a multi-core processor having one or more cores to read and execute separate instructions. The processors may include general purpose processors, application specific integrated circuits (ASICs), field programmable gate arrays (FPGAs), other integrated circuits.

The memory 1616 may include any tangible medium for short-term or long-term storage for data and/or processor executable instructions, according to embodiments. The memory 1716 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc. In embodiments, system 1600 may be used to control activation of a light source and/or various flow control devices, pumps, valves, etc. of a fluid treatment system. Memory 1616 can store protocols 1620 and procedures 1624, such as protocols and procedures for introducing fluid into a flow cell and/or illuminating fluid in a flow cell, which would control operation of pumps, valves, clamping mechanisms, illuminators etc.

Storage 1628 may be any long-term data storage device or component. Storage 1620 may include one or more of the systems described in above with respect to memory 1616, according to embodiments. Storage 1628 may be permanent or removable. In embodiments, system 1600 is part of a system for treating a fluid and storage 1628 may store various procedures for utilizing the system to treat fluids, e.g., pathogen reduce a fluid or photopheresis, which may include values for different treatment processes.

Computer system 1600 also includes communication devices 1636. Devices 1636 may allow system 1600 to communicate over networks, e.g., wide area networks, local area networks, storage area networks, etc., and may include a number of devices such as modems, hubs, network interface cards, wireless network interface cards, routers, switches, bridges, gateways, wireless access points, etc.

It may be apparent to those skilled in the art that various modifications and variations can be made to the embodiments of the present invention described above without departing from their scope. Thus, it should be understood that the invention is not to be limited to the specific examples given, the embodiments described, or the embodiments shown in the figures. Rather, the invention is intended to cover modifications and variations.

While example embodiments and applications of the present invention have been illustrated and described, it is to be understood that the invention is not limited to the precise configuration, steps, and structures described above. Various modifications, changes, and variations apparent to those skilled in the art may be made in the arrangement, operation, and details of the methods and systems of the present invention disclosed herein without departing from the scope of the invention.

What is claimed is:

1. A method of treating a fluid, the method comprising:
   introducing a first flow of fluid into a first channel of a flow cell through an inlet port, the first channel defined by a first continuous wall having a first cross-section including at least a first dimension;
   separating at a first separation zone of the flow cell the first flow of fluid into a second flow of fluid in a second channel of the flow cell and a third flow of fluid in a third channel of the flow cell, the second channel extending from the first channel at a right angle, the second channel defined by a second continuous wall and the third channel defined by a third continuous wall that is different from the second continuous wall, the first continuous wall splitting into the second continuous wall and the third continuous wall in the first separation zone;
   reorienting at least the second flow of fluid in the second channel in a first reorienting zone including areas of both the second channel and the third channel, the second channel changes direction at least once to reorientate the second flow of fluid;
   recombining the second flow of fluid with the third flow of fluid in a first recombining zone where the second channel and the third channel merge from different directions into a fourth channel of the flow cell defined by a fourth continuous wall to form a fourth flow of fluid;
   separating at a second separation zone of the flow cell the fourth flow of fluid into a fifth flow of fluid in a fifth channel of the flow cell and a sixth flow of fluid in a sixth channel of the flow cell, the fifth channel extending from the fourth channel at a right angle relative to the fourth channel, the fifth channel defined by a fifth continuous wall and the sixth channel defined by a sixth continuous wall that is different from the fifth continuous wall, the fourth continuous wall splitting into the fifth continuous wall and the sixth continuous wall in the second separation zone;
   reorienting at least the fifth flow of fluid in the fifth channel in a second reorientating zone including areas of both the fifth channel and the sixth channel, the fifth channel changes direction at least once to reorientate the fifth flow of fluid;
   recombining the fifth flow of fluid with the sixth flow of fluid in a second recombining zone where the fifth channel and the sixth channel merge from different directions into a seventh channel of the flow cell defined by a seventh continuous wall to form a seventh flow of fluid; and
   treating with electromagnetic energy one or more of the first flow of fluid, the second flow of fluid, the third flow of fluid, the fourth flow of fluid, the fifth flow of fluid, the sixth flow of fluid, or seventh flow of fluid;
   wherein the first continuous wall splits into the second continuous wall and the third continuous wall in the first separation zone, and the second continuous wall and the third continuous wall merge into the fourth continuous wall in the first recombining zone;
   wherein the fourth continuous wall splits into the fifth continuous wall and the sixth continuous wall in the second separation zone, and the fifth continuous wall and the sixth continuous wall merge into the seventh continuous wall in the second recombining zone;
   wherein the first channel, the second channel, the third channel, the fourth channel, the fifth channel, the sixth channel, and the seventh channel are together configured to direct the fluid through all three dimensions of a three-dimensional space; and
   wherein at least one of the first separation zone, the second separation zone, the first reorienting zone, the second reorienting zone, the first recombining zone, and the second recombining zone are substantially transmissive to a form of electromagnetic energy.

2. The method of claim 1, wherein the reorienting at least the second flow of fluid comprises changing the second flow of fluid from a first direction to a second direction.

3. The method of claim 2, wherein the reorienting at least the second flow of fluid further comprises changing the second flow of fluid from the second direction to a third direction.

4. The method of claim 1, wherein the recombining the second flow of fluid with the third flow of fluid comprises stacking the second flow of fluid with the third flow of fluid.

5. The method of claim 1, wherein the recombining the second flow of fluid with the third flow of fluid comprises folding the second flow of fluid with the third flow of fluid.

6. The method of claim 1, wherein the reorienting at least the fifth flow of fluid comprises changing the fifth flow of fluid from a fourth direction to a fifth direction.

7. The method of claim 6, wherein the reorienting at least the fifth flow of fluid further comprises changing the fifth flow of fluid from the fifth direction to a sixth direction.

8. The method of claim 1, wherein the recombining the fifth flow of fluid with the sixth flow of fluid comprises stacking the fifth flow of fluid with the sixth flow of fluid.

9. The method of claim 1, wherein the recombining the fifth flow of fluid with the sixth flow of fluid comprises folding the fifth flow of fluid with the sixth flow of fluid.

10. The method of claim 1, wherein the fluid comprises a biological fluid.

11. The method of claim 10, wherein the fluid comprises blood.

12. The method of claim 10, wherein the fluid comprises one or more components of blood.

13. The method of claim 1, wherein the fluid comprises a photosensitizer.

14. The method of claim 1, wherein the electromagnetic energy comprises light.

15. The method of claim 14, wherein the light comprises a wavelength in the ultraviolet spectrum.

16. The method of claim 14, wherein the light comprises a wavelength in the visible light spectrum.

17. The method of claim 1, wherein the treating comprises exposing to electromagnetic energy from a plurality of directions.

* * * * *